United States Patent
Yang et al.

(10) Patent No.: US 10,351,706 B2
(45) Date of Patent: Jul. 16, 2019

(54) NEAR-INFRARED FLUORESCENT DYES AND USES THEREOF

(71) Applicant: East China University of Science and Technology, Shanghai (CN)

(72) Inventors: Youjun Yang, Shanghai (CN); Xinran Li, Shanghai (CN); Zuhai Lei, Shanghai (CN); Yi Li, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 15/756,734

(22) PCT Filed: Aug. 30, 2016

(86) PCT No.: PCT/CN2016/097271
§ 371 (c)(1),
(2) Date: Mar. 1, 2018

(87) PCT Pub. No.: WO2017/036377
PCT Pub. Date: Mar. 9, 2017

(65) Prior Publication Data
US 2018/0291206 A1    Oct. 11, 2018

(30) Foreign Application Priority Data
Sep. 1, 2015 (CN) .......................... 2015 1 0552618

(51) Int. Cl.
| | |
|---|---|
| *C07D 491/22* | (2006.01) |
| *C07D 311/96* | (2006.01) |
| *C09K 11/06* | (2006.01) |
| *C09B 11/10* | (2006.01) |
| *C07D 491/20* | (2006.01) |
| *C09B 11/24* | (2006.01) |
| *C09B 23/01* | (2006.01) |

(52) U.S. Cl.
CPC ............ *C09B 11/10* (2013.01); *C07D 311/96* (2013.01); *C07D 491/20* (2013.01); *C09B 11/24* (2013.01);
(Continued)

(58) Field of Classification Search
CPC .. C07D 491/22; C07D 491/20; C07D 311/96; C09B 57/00; C09K 11/06
USPC .......... 546/15, 28, 36; 549/331; 252/301.26
See application file for complete search history.

(56) References Cited

FOREIGN PATENT DOCUMENTS

| WO | 2008011508 | 1/2008 |
|---|---|---|
| WO | 2008109464 | 9/2008 |
| WO | 2009036351 | 3/2009 |
| WO | 2013003812 | 1/2013 |

OTHER PUBLICATIONS

International Search Report and Written Opinion issued in International Application No. PCT/CN2016/097271 dated Dec. 1, 2016 (5 pages).

*Primary Examiner* — Charanjit Aulakh
(74) *Attorney, Agent, or Firm* — Hamre, Schumann, Mueller & Larson, P.C.

(57) ABSTRACT

The invention relates to a near-infrared fluorescent dye and use thereof, and particularly relates to compounds represented by following Formulae A, B and C, wherein each group in the Formulae is described in the specification. Further provided are a dye composition comprising the compound represented by Formula A or Formula B, and a preparation method of the compound represented by Formula A or Formula B. The compound has a maximum absorption wavelength of 880 nm, considerably exceeding maximum absorption wavelengths of the majority of small-molecule near-infrared fluorescent dyes in the prior art. Moreover, the structure thereof does not aggregate even if the concentration thereof is excessively high, thereby having considerably high chemical stability and light stability.

Formula A

Formula B (Continued)

-continued
Formula C
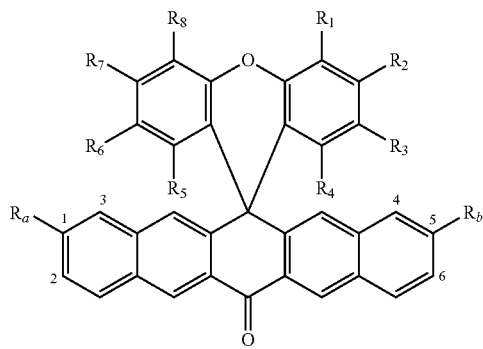
22 Claims, 2 Drawing Sheets
(52) U.S. Cl.
CPC ...... *C09B 23/0025* (2013.01); *C09B 23/0066* (2013.01); *C09K 11/06* (2013.01); C09K 2211/1018 (2013.01)

NEAR-INFRARED FLUORESCENT DYES AND USES THEREOF

TECHNICAL FIELD

The present disclosure relates to a field of fluorescent dye, specifically relates to near-infrared fluorescent dyes and uses thereof.

BACKGROUND

In recent years, the development of new near infrared long wavelength dyes is a hot research trend in the field of dye chemistry. Such materials are widely used in near-infrared fluorescence imaging, photoacoustic imaging, photothermal therapy, photodynamic therapy, near infrared shielding, solar photosensitive cells, and the like. Near infrared dyes in the literature mainly include cyanine dyes, squaraine dyes, BODIPY dyes, phthalocyanine dyes, etc. The absorption wavelength of these small molecule dyes generally located at the blue region of the near infrared band, i.e., between 650 and 800 nm. Some organic small molecule dyes with longer absorption wavelength are often not suitable for practical applications because of poor stability and poor solubility, etc. In recent years, some organic molecules with large conjugated structures have also been found to have absorption in the near infrared region. However, due to the large conjugated structure, difficult synthesis, difficult modification and high tendency to aggregate, etc., of these dyes, they have not been used in practical applications. In order to meet the need of long-wavelength dyes in the fields of biomedical and material, it is very important to develop new parent cores for near-infrared dye.

SUMMARY

Provided in the present disclosure are a series of novel parent core structures for fluorescent dyes, which are expected to be widely used in the above fields. First of all, the maximum absorption wavelength of these dyes is 880 nm, far exceeding the maximum absorption wavelength of most existing small-molecular near-infrared fluorescent dyes. Secondly, these dye structures do not aggregate even at very high concentrations. In addition, these dyes have very high chemical and light stability.

In the first aspect, the present disclosure provides a compound of the following Formula A:

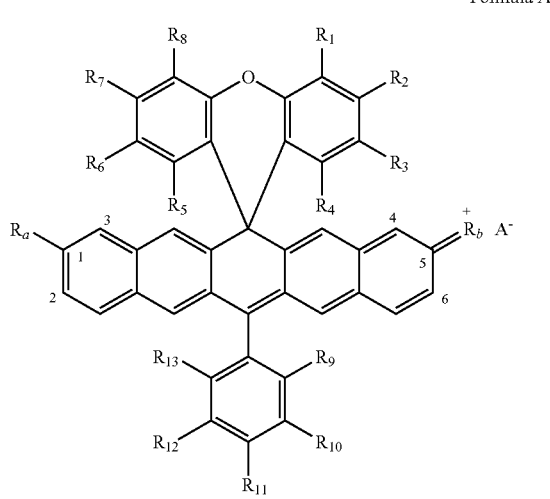

Formula A wherein:
$R_a$ is $NR_{14}R_{15}$;
$R_b$ is $NR_{14}R_{15}$;
$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl, C2-4 alkenyl, $-SO_3^-$, $-SO_2X$, $-SO_2NH_2$, nitro, and C1-4 alkyl optionally substituted by one or two substituents selected from the group consisting of C1-4 alkoxyl, halogen, azido, amino and thiol;
$R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle;
X is halogen; and
$A^-$ is selected from the group consisting of $F^-$, $Cl^-$, $Br^-$, $I^-$, $OAc^-$, $HSO_4^-$, $ClO_4^-$, $F_3CCOO^-$, $CH_3SO_3^-$, $CF_3SO_3^-$, $BF_4^-$, $PF_6^-$ and $NO_3^-$.

In a specific embodiment, $R_1$, $R_2$, $R_3$ and $R_4$ are each independently selected from the group consisting of H, $-SO_3^-$, $-SO_2X$ and halogen; $R_5$, $R_6$, $R_7$ and $R_8$ are each independently selected from the group consisting of H, $-SO_3^-$, $-SO_2X$ and halogen; $R_9$, $R_{10}$, $R_{11}$, $R_{12}$ and $R_{13}$ are each independently selected from the group consisting of H, $-SO_3^-$, $-SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol.

In a specific embodiment, $R_1$, $R_2$, $R_4$, $R_5$, $R_7$, $R_8$, $R_{10}$ and $R_{11}$ are H; $R_3$ is selected from the group consisting of H, $-SO_3^-$, $-SO_2X$ and halogen; $R_6$ is selected from the group consisting of H, $-SO_3^-$, $-SO_2X$ and halogen; $R_9$ is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ is selected from the group consisting of H, $-SO_3^-$, $-SO_2X$ and halogen; and $R_{13}$ is selected from the group consisting of H and C1-4 alkyl.

In a specific embodiment, the compound of Formula A has a structure as shown in the following Formula AI:

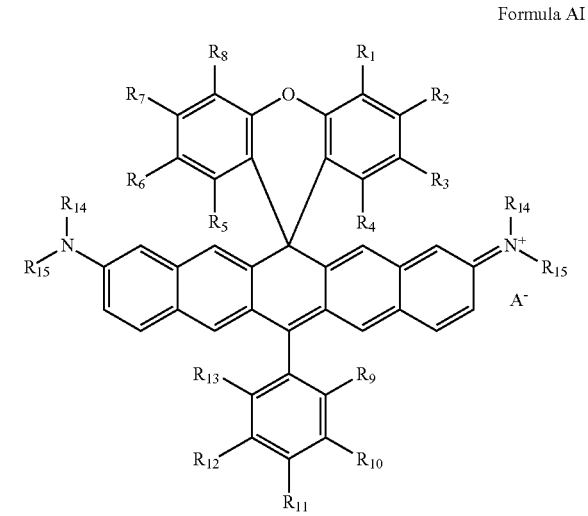

Formula AI wherein:

$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-6 alkoxyl, halogen, cyano, carboxyl, C2-4 alkenyl, —$SO_3^-$, —$SO_2X$, —$SO_2NH_2$, nitro and C1-4 alkyl optionally substituted by one or two substituents selected from the group consisting of C1-6 alkoxyl, halogen, azido, amino and thiol; and $R_{14}$ and $R_{15}$ are each independently selected from the group consisting of C1-6 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle.

In a specific embodiment, $R_1$, $R_2$, $R_3$, $R_4$, $R_5$, $R_6$, $R_7$, $R_8$, $R_9$, $R_{10}$, $R_{11}$, $R_{12}$ are $R_{13}$ are all H, $R_{14}$ and $R_{15}$ are each independently selected from the group consisting of C1-6 alkyl.

In a specific embodiment, both of $R_{14}$ and $R_{15}$ are C1-4 alkyl.

In a specific embodiment, $R_{14}$ is C1-4 alkyl; $R_{15}$ is C2-4 alkenyl.

In a specific embodiment, $R_{14}$ is independently C1-4 alkyl, and two $R_{15}$ form two 6-membered nitrogen-containing heterocycles, respectively together with N, C1 and C2; and N, C5 and C6 to which they attach.

In a specific embodiment, two $R_{14}$ forms two 6-membered nitrogen-containing heterocycle, respectively together with N, C1 and C3; and N, C4 and C5 to which they attach, and two $R_{15}$ form two 6-membered nitrogen-containing heterocycles, respectively together with N, C1 and C2; and N, C5 and C6 to which they attach.

In a specific embodiment, $R_1$, $R_2$, $R_3$ and $R_4$ are each independently selected from the group consisting of H, —$SO_3^-$, —$SO_2X$ and halogen; $R_5$, $R_6$, $R_7$ and $R_8$ are each independently selected from the group consisting of H, —$SO_3^-$, —$SO_2X$ and halogen; $R_9$, $R_{10}$, $R_{11}$, $R_{12}$ and $R_{13}$ are each independently selected from the group consisting of H, —$SO_3^-$, —$SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol.

In a specific embodiment, $R_{14}$ and $R_{15}$ are each independently selected from the group consisting of C1-4 alkyl and C2-4 alkenyl; $R_1$, $R_2$, $R_3$ and $R_4$ are each independently selected from the group consisting of H, —$SO_3^-$, —$SO_2X$ and halogen; $R_5$, $R_6$, $R_7$ and $R_8$ are each independently selected from the group consisting of H, —$SO_3^-$, —$SO_2X$ and halogen; $R_9$, $R_{10}$, $R_{11}$, $R_{12}$ and $R_{13}$ are each independently selected from the group consisting of H, —$SO_3^-$, —$SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol.

In a specific embodiment, $R_{14}$ and $R_{15}$ are each independently selected from the group consisting of C1-4 alkyl and C2-4 alkenyl; $R_1$, $R_2$, $R_4$, $R_5$, $R_7$, $R_8$, $R_{10}$ and $R_{11}$ are H; $R_3$ is selected from the group consisting of H, —$SO_3^-$, —$SO_2X$ and halogen; $R_6$ is selected from the group consisting of H, —$SO_3^-$, —$SO_2X$ and halogen; $R_9$ is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ is selected from the group consisting of H, —$SO_3^-$, —$SO_2X$ and halogen; and $R_{13}$ is selected from the group consisting of H and C1-4 alkyl.

In a specific embodiment, $R_{14}$ and $R_{15}$ are each independently selected from the group consisting of C1-4 alkyl and C2-4 alkenyl; $R_1$, $R_2$, $R_3$, $R_4$, $R_5$, $R_6$, $R_7$, $R_8$, $R_9$, $R_{10}$, $R_{11}$, $R_{12}$ and $R_{13}$ are all H; $R_9$ is selected from the group consisting of H and C1-4 alkyl optionally substituted by one or two substituents selected from the group consisting of C1-4 alkoxyl and halogen.

In a specific embodiment, $R_1$, $R_2$, $R_4$, $R_5$, $R_7$, $R_8$, $R_{10}$ and $R_{11}$ are all H; $R_3$, $R_6$ and $R_{12}$ are each independently selected from the group consisting of H and —$SO_3^-$; $R_9$ is selected from the group consisting of H, C1-C4 alkyl and C1-C4 alkoxyl; $R_{13}$ is selected from the group consisting of H and C1-C4 alkyl; $R_{14}$, together with N, C1 and C3 to which it attaches or together with N, C4 and C5 to which it attaches, forms a 6-membered nitrogen-containing heterocycle; and $R_{15}$, together with N, C1 and C2 to which it attaches or N, C5 and C6 to which it attaches, forms a 6-membered nitrogen-containing heterocycle.

In a specific embodiment, the compound of Formula A has a structure as shown in the following Formula AII:

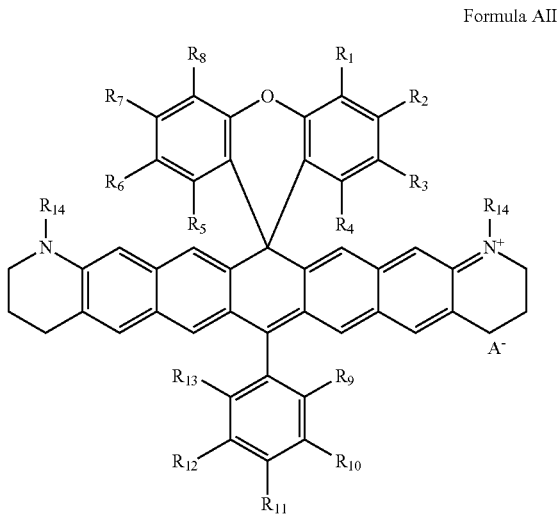

Formula AII wherein:

$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-C6 alkoxyl, halogen, cyano, carboxyl, C2-4 alkenyl, —$SO_3^-$, —$SO_2X$, —$SO_2NH_2$, nitro and C1-6 alkyl optionally substituted by one or two substituents selected from the group consisting of C1-4 alkoxyl, halogen, azido, amino and thiol; and $R_{14}$ is independently selected from the group consisting of C1-6 alkyl.

In a specific embodiment of Formula AII, $R_1$, $R_2$, $R_3$ and $R_4$ are each independently selected from the group consisting of H, —$SO_3^-$, —$SO_2X$ and halogen; $R_5$, $R_6$, $R_7$ and $R_8$ are each independently selected from the group consisting of H, —$SO_3^-$, —$SO_2X$ and halogen; $R_9$, $R_{10}$, $R_{11}$, $R_{12}$ and $R_{13}$ are each independently selected from the group consisting of H, —$SO_3^-$, —$SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol.

In a specific embodiment of Formula AII, $R_1$, $R_2$, $R_3$, $R_4$, $R_5$, $R_6$, $R_7$ and R are H; $R_9$, $R_{10}$, $R_{11}$, $R_{12}$ and $R_{13}$ are each independently selected from the group consisting of H and C1-4 alkyl.

In a specific embodiment of Formula AII, $R_1$, $R_2$, $R_3$, $R_4$, $R_4$, $R_6$, $R_7$, $R_8$, $R_{10}$, $R_{11}$, $R_{12}$ and $R_{13}$ are H; $R_9$ is selected from the group consisting of H and C1-4 alkyl.

In a specific embodiment, the compound of Formula A has a structure as shown in the following Formula AIII:

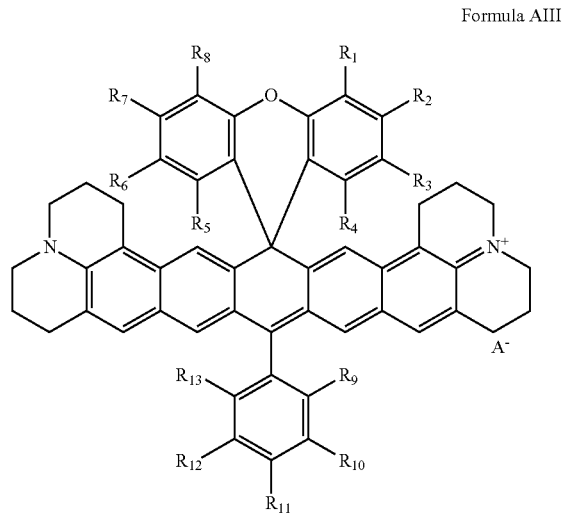

Formula AIII wherein:

$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-C6 alkoxyl, halogen, cyano, carboxyl, C2-4 alkenyl, $-SO_3^-$, $-SO_2X$, $-SO_2NH_2$, nitro and C1-6 alkyl optionally substituted by one or two substituents selected from the group consisting of C1-4 alkoxyl, halogen, azido, amino and thiol.

In a specific embodiment of Formula AIII, $R_1$, $R_2$, $R_3$ and $R_4$ are each independently selected from the group consisting of H, $-SO_3^-$, $-SO_2X$ and halogen; $R_5$, $R_6$, $R_7$ and $R_8$ are each independently selected from the group consisting of H, $-SO_3^-$, $-SO_2X$ and halogen; $R_9$, $R_{10}$, $R_{11}$, $R_{12}$ and $R_{13}$ are each independently selected from the group consisting of H, $-SO_3^-$, $-SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol.

In a specific embodiment of Formula AIII, $R_1$, $R_2$, $R_4$, $R_5$, $R_7$, $R_8$, $R_{10}$ and $R_{11}$ are H $R_3$ is selected from the group consisting of H, $-SO_3^-$, $-SO_2X$ and halogen; $R_6$ is selected from the group consisting of H, $-SO_3^-$, $-SO_2X$ and halogen; $R_9$ is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ is selected from the group consisting of H, $-SO_3^-$, $-SO_2X$ and halogen; and $R_{13}$ is selected from the group consisting of H and C1-4 alkyl.

In a second aspect, the present disclosure provides a compound of Formula B:

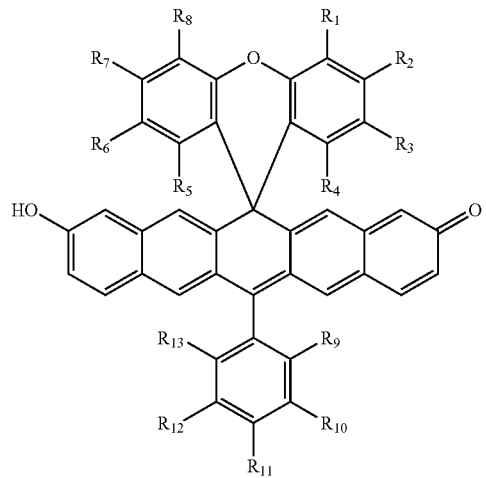

Formula B wherein, $R_1$, $R_2$, $R_3$, $R_4$, $R_5$, $R_7$, $R_8$, $R_9$, $R_{10}$, $R_{11}$, $R_{12}$ and $R_{13}$ are each independently selected from the group consisting of H, hydroxyl, amino, C1-C6 alkoxyl, halogen, cyano, carboxyl, C2-4 alkenyl, $-SO_3^-$, $-SO_2X$, $-SO_2NH_2$, nitro and C1-6 alkyl optionally substituted by one or two substituents selected from the group consisting of C1-4 alkoxyl, halogen, azido, amino and thiol.

In a specific embodiment of Formula B, $R_1$, $R_2$, $R_3$ and $R_4$ are each independently selected from the group consisting of H, $-SO_3^-$, $-SO_2X$ and halogen; $R_5$, $R_6$, $R_7$ and $R_8$ are each independently selected from the group consisting of H, $-SO_3^-$, $-SO_2X$ and halogen; $R_9$, $R_{10}$, $R_{11}$, $R_{12}$ and $R_{13}$ are each independently selected from the group consisting of H, $-SO_3^-$, $-SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol.

In a specific embodiment of Formula B, $R_1$, $R_2$, $R_3$, $R_4$, $R_5$, $R_6$, $R_7$ and $R_8$ are H; $R_9$, $R_{10}$, $R_{11}$, $R_{12}$ and $R_{13}$ are each independently selected from the group consisting of H, carboxyl and C1-4 alkyl.

In a specific embodiment of Formula B, $R_1$, $R_2$, $R_3$, $R_4$, $R_5$, $R_6$, $R_7$, $R_8$, $R_{10}$, $R_{11}$, $R_{12}$ and $R_{13}$ are H; $R_9$ is selected from the group of H, carboxyl and C1-4 alkyl.

In a specific embodiment, the compound of the present disclosure is selected from the group consisting of 1a-1f, 2a-2b, 3a-3n and 4a-4c.

The present disclosure also provides a compound of Formula C:

Formula C

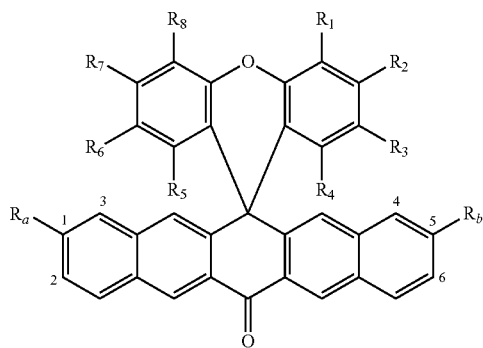

wherein, $R_a$ or $R_b$ is $OR_{14}$ or $NR_{14}R_{15}$;

$R_1$, $R_2$, $R_3$, $R_4$, $R_5$, $R_6$, $R_7$ and $R_8$ are each independently selected from the group consisting of H, hydroxyl, amino, C1-4 alkoxyl, halogen, cyano, carboxyl, C2-4 alkenyl, $—SO_3^-$, $—SO_2X$, $—SO_2NH_2$, nitro and C1-4 alkyl optionally substituted by one or two substituents selected from the group consisting of C1-4 alkoxyl, halogen, azido, amino and thiol; and $R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle.

Examples of Formula C include the following Formulae CI, CII, CIII and CIV:

Formula CI

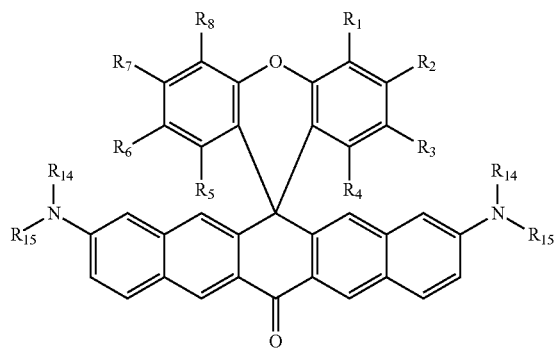

Formula CII

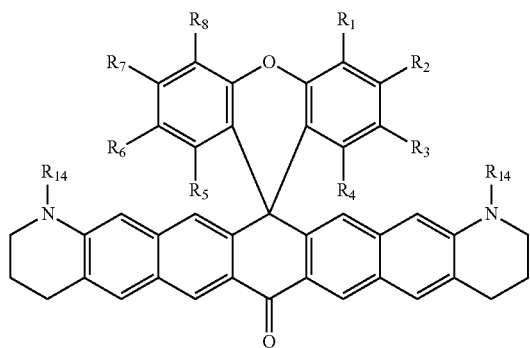

Formula CIII

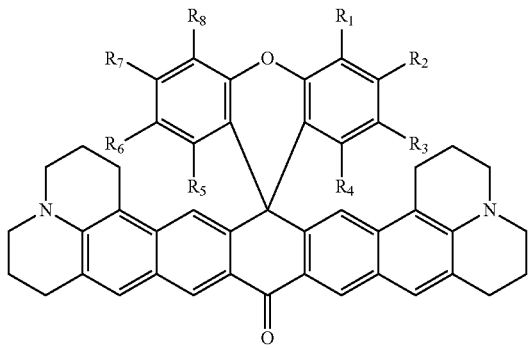

Formula CIV

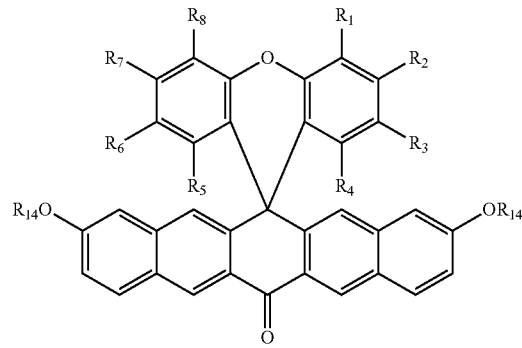

wherein $R_1$, $R_2$, $R_3$, $R_4$, $R_5$, $R_6$, $R_7$, $R_8$, $R_{14}$ and $R_{15}$ are those as defined in each of the previous embodiments.

The present disclosure also provides a method for producing a compound of Formula A or Formula B, comprising carrying out an addition reaction between a compound of Formula C and a compound of the following Formula C8 in an ether solvent, thereby producing the compound of Formula A; or reacting a compound of Formula C with a compound of the following Formula C8 in an ether solvent and then treating the product by an acid to produce the compound of Formula B:

Formula C8

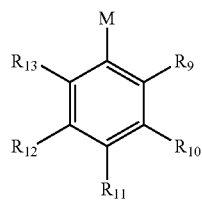

wherein in Formula C8, $R_9$, $R_{10}$, $R_{11}$, $R_{12}$ and $R_{13}$ are those as defined in any of the previous embodiments, and M is Li or MgBr.

In a specific embodiment, the ether solvent is ethyl ether, tetrahydrofuran, dioxane or a mixture thereof.

In a specific embodiment, the acid is selected from the group consisting of protonic acid and Lewis acid, such as HBr, HI, $BBr_3$ and $AlCl_3$.

In a specific embodiment, a compound of the following Formula D8 is heated in an aqueous solution of an acid to produce a compound of Formula C:

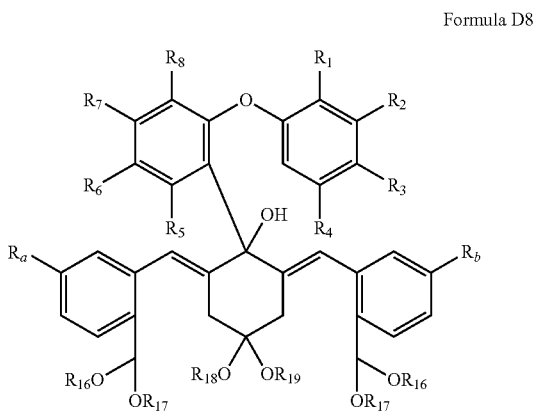

Formula D8

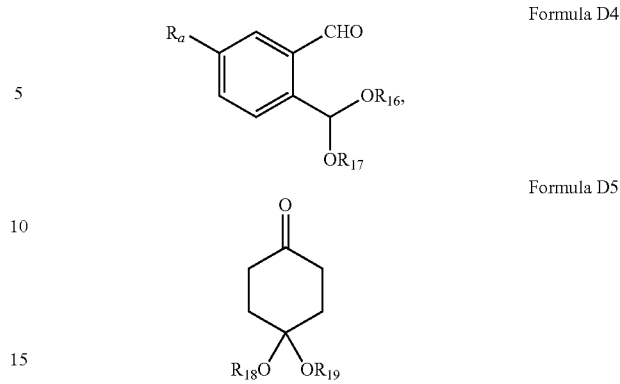

Formula D4

Formula D5 wherein $R_1$, $R_2$, $R_3$, $R_4$, $R_5$, $R_6$, $R_7$, $R_5$, $R_a$ and $R_b$ are those as defined in any of the previous embodiments; $R_{16}$ and $R_{17}$ are each C1-4 alkyl, or link together to form —$CH_2CH_2$—, —$CH_2CH_2CH_2$— or —$CH_2C(CH_3)_2CH_2$—; $R_{18}$ and $R_{19}$ are each C1-4 alkyl, or link together to form —$CH_2CH_2$—, —$CH_2CH_2CH_2$— or —$CH_2C(CH_3)_2CH_2$—.

In a specific embodiment, the acid is a concentrated hydrochloric acid, and the compound of the following Formula D8 is heated to a temperature of 50-70° C., such as 60° C.

In a specific embodiment, a compound of the following Formula D6 is reacted with a compound of Formula D7 in an ether solvent to produce a compound of Formula D8:

Formula D6

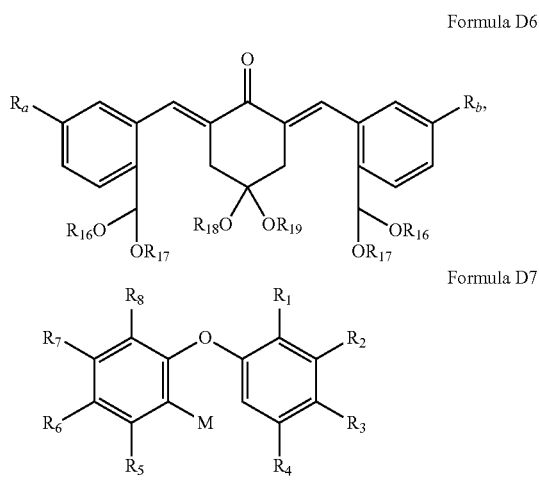

Formula D7 wherein in Formula D6, $R_a$ and $R_b$ are those as defined in any of the previous embodiments; $R_{16}$ and $R_{17}$ are each C1-4 alkyl, or link together to form —$CH_2CH_2$—, —$CH_2CH_2CH_2$— or —$CH_2C(CH_3)_2CH_2$—; $R_{18}$ and $R_{19}$ are each C1-4 alkyl, or link together to form —$CH_2CH_2$—,——$CH_2CH_2CH_2$— or —$CH_2C(CH_3)_2CH_2$—; in Formula D7, $R_1$, $R_2$, $R_3$, $R_4$, $R_5$, $R_6$, $R_7$ and $R_8$ are those as defined in any of the previous embodiments, M is Li or MgBr.

In a specific embodiment, a compound of Formula D4 is reacted with a compound of Formula D5 in an aqueous solution of a base to prepare a compound of Formula D6:

wherein $R_a$, $R_{16}$, $R_{17}$, $R_{18}$ and $R_{19}$ are those as defined in any of the previous embodiments.

In a specific embodiment, the aqueous solution of the base is concentrated NaOH solution or concentrated KOH solution.

DESCRIPTIONS OF DRAWINGS

Figure 1:
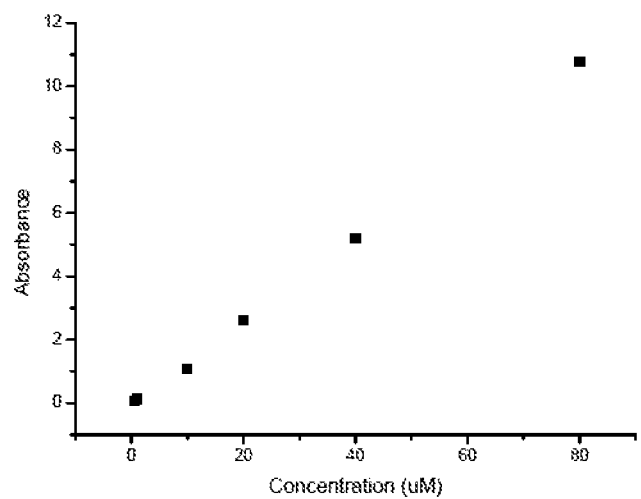
FIG. 1 shows a change of the UV-visible absorbance of dye 3d in chloroform in terms of its concentration. Data were collected by Shimadzu UV 2600 UV-Vis spectrometer.
Figure 2:
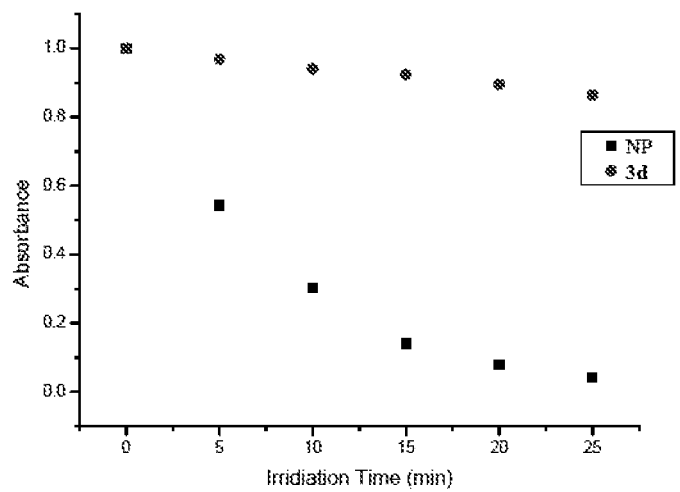
FIG. 2 shows photostability of dye 3d, in which the solid circle (●) indicates a change of the UV-visible absorbance of dye 3d in terms of irradiation time, and the solid block (■) indicates a change of the UV-visible absorbance of a control compound (CAS: 116453-73-7) in terms of irradiation time. Data were collected by Shimadzu UV 2600 UV-Vis spectrometer.
Figure 3:
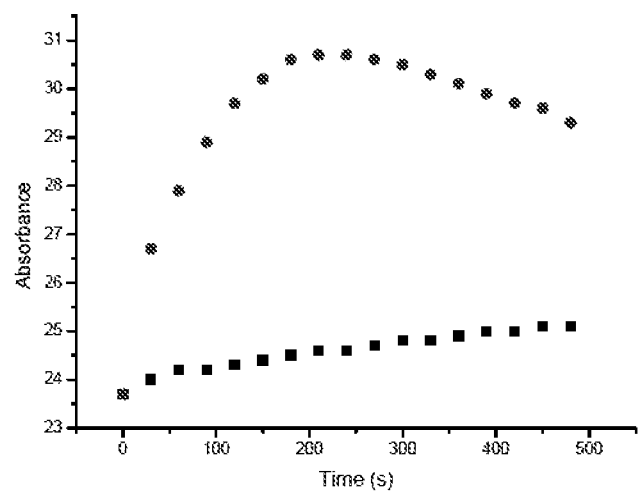
FIG. 3 shows photothermal conversion capacity of dye 3d, in which the solid circle (●) indicates a change of temperature of an aqueous solution of dye 3d in terms of illumination, and the solid block (■) indicates a change of temperature of an aqueous solution under the same illumination. The lamp used for experiment was a 350 watt halogen lamp.
Figure 4:
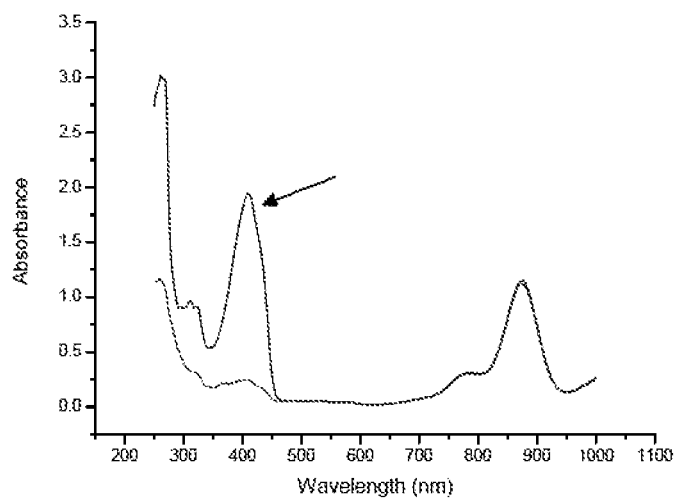

FIG. 4 shows the photosensitive capacity of dye 3d, in which the black curve (the curve referred by the arrow) indicates the UV-visible absorbance of a mixture solution of dye 3d and singlet oxygen detection reagent (CAS: 5471-63-6). After illumination at 880 nm, the peak at 400 nm disappeared, indicating that singlet oxygen was generated in the system. Data were collected by Shimadzu UV2600 UV-Vis spectrometer.

DETAILED DESCRIPTION

As used herein, the term "alkyl" includes a straight and linear alkyl of generally 1-6 carbon atoms, preferably 1-4 carbon atoms. Examples of alkyl include methyl, ethyl, propyl, n-butyl, iso-butyl and t-butyl etc.

As used herein, the term "X" in the group —$SO_2X$ is halogen.

As used herein, the term "halogen" refers to fluoro, chloro, bromo and iodine, generally refers to fluoro, chloro and bromo.

Although in the Examples of the present disclosure the compound of the present invention formed a complex with $Br^-$, it should be understood that the compound of Formula A can form a complex with other anions, such as F⁻, Cl⁻, I⁻, OAc⁻, HSO₄⁻, ClO₄⁻, F₃CCOO⁻, CH₃SO₃⁻, CF₃SO₃⁻, BF₄⁻, PF₆⁻ or NO₃⁻, etc.

It should be understood that, in various structural Formulae of the present disclosure, i.e., in Formulae A, AAII, AIII, B, C, CI, CII, CIII, CIV, D1, D2, D3, D4, D5, D6, D7, D8 and C8, $R_1$-$R_{19}$, $R_a$ and $R_b$ may be selected from the groups as described in any of the previous embodiments.

Specifically, in all of these structural Formulae, if present, $R_a$ is $NR_{14}R_{15}$; $R_b$ is $NR_{14}R_{15}$; $R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl C2-4 alkenyl, —SO₃⁻, —SO₂X, —SO₂NH₂, nitro and C1-4 alkyl optionally substituted by one or two substituents selected from the group consisting of C1-4 alkoxyl, halogen, azido, amino and thiol; $R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle; X is halogen; $R_{16}$-$R_{19}$ are each independently C1-4 alkyl, or $R_{16}$ links with $R_{17}$ to form —CH₂CH₂—, —CH₂CH₂CH₂- or —CH₂C(CH₃)₂CH₂, and/or $R_{15}$ links with $R_{14}$ to form —CH₂CH₂, —CH₂CH₂CH₂— or —CH₂C(CH₃)CH₂—.

Preferably, in all of these structural Formulae, if present, preferably $R_1$, $R_2$, $R_3$ and $R_4$ are each independently selected from the group consisting of H, —SO₃⁻, —SO₂X and halogen; preferably $R_5$, $R_6$, $R_7$ and $R_8$ are each independently selected from the group consisting of H, —SO₃⁻, —SO₂X and halogen; preferably $R_9$, $R_{10}$, $R_{11}$, $R_{12}$ and $R_{13}$ are each independently selected from the group consisting of H, —SO₃⁻, —SO₂X, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol; preferably $R_{16}$ links with $R_{17}$ to form —CH₂CH₂—, —CH₂CH₂CH₂— and —CH₂C(CH₃)₂CH₂—; preferably $R_{18}$ links with $R_{19}$ to form —CH₂CH₂—, —CH₂CH₂CH₂— or —CH₂C(CH₃)₂CH₂—.

More preferably, in all these structural Formulae, if present, $R_1$, $R_2$, $R_4$, $R_5$, $R_7$, $R_8$, $R_{10}$ and $R_{11}$ preferably are H; $R_3$ preferably is selected from the group consisting of H, —SO₃⁻, —SO₂X and halogen; $R_6$ preferably is selected from the group consisting of H, —SO₃⁻, —SO₂X and halogen; $R_9$ preferably is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ preferably is selected from the group consisting of H, —SO₃⁻, —SO₂X and halogen $R_{13}$ preferably is selected from the group consisting of H and C1-4 alkyl.

It should be understood that the present disclosure comprises any combination of the above preferred groups.

The compounds of the present disclosure has a novel parent core for fluorescent dye, and the maximum absorption wavelength of these compounds is about 880 nm, which greatly exceeds the maximum absorption wavelength of most existing small-molecule near-infrared fluorescent dyes. Moreover, these compounds are not aggregated even under very high concentration, and they have very high chemical stability and photostability. Therefore, the compounds of the present disclosure have a wide range of applications in near-infrared fluorescence imaging, photothermal therapy, photodynamic therapy, solar photosensitive cells, and the like.

Therefore, the present disclosure further provides a dye composition, which comprises a compound of the present disclosure and a solvent. Solvents suitable for used in the present disclosure include, but are not limited to, one or more of MeOH, EtOH, PrOH, iPrOH, BuOH, acetone, DMF, DMSO, pyridine, DCM, chloroform, dichloroethane, MeCN, benzene, toluene, p-xylene, chlorobenzene, nitrobenzene, 1,4-dioxane, THF, ethyl acetate and AcOH.

A general synthetic scheme for a compound of Formulae C, B or A is shown below:

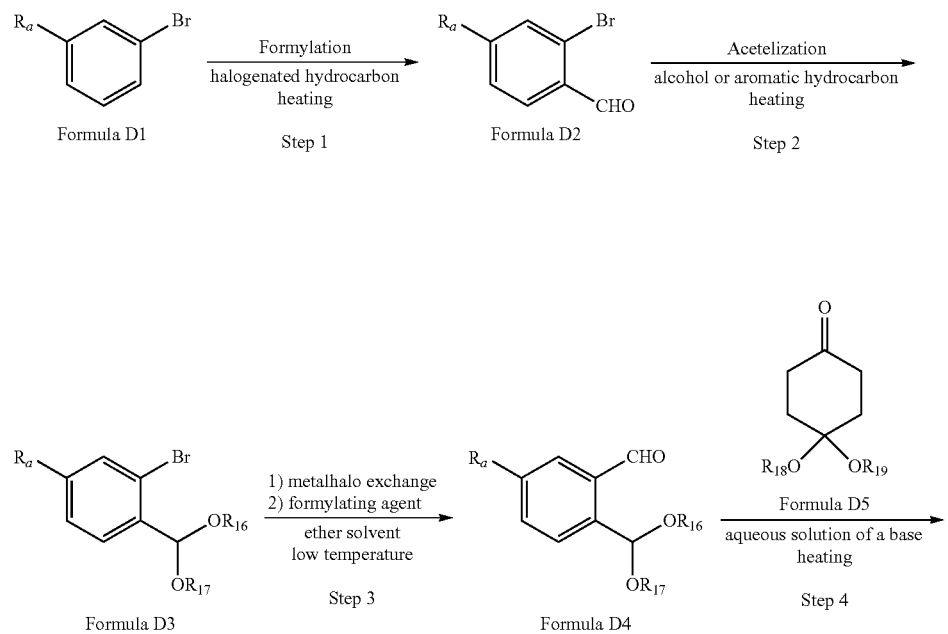

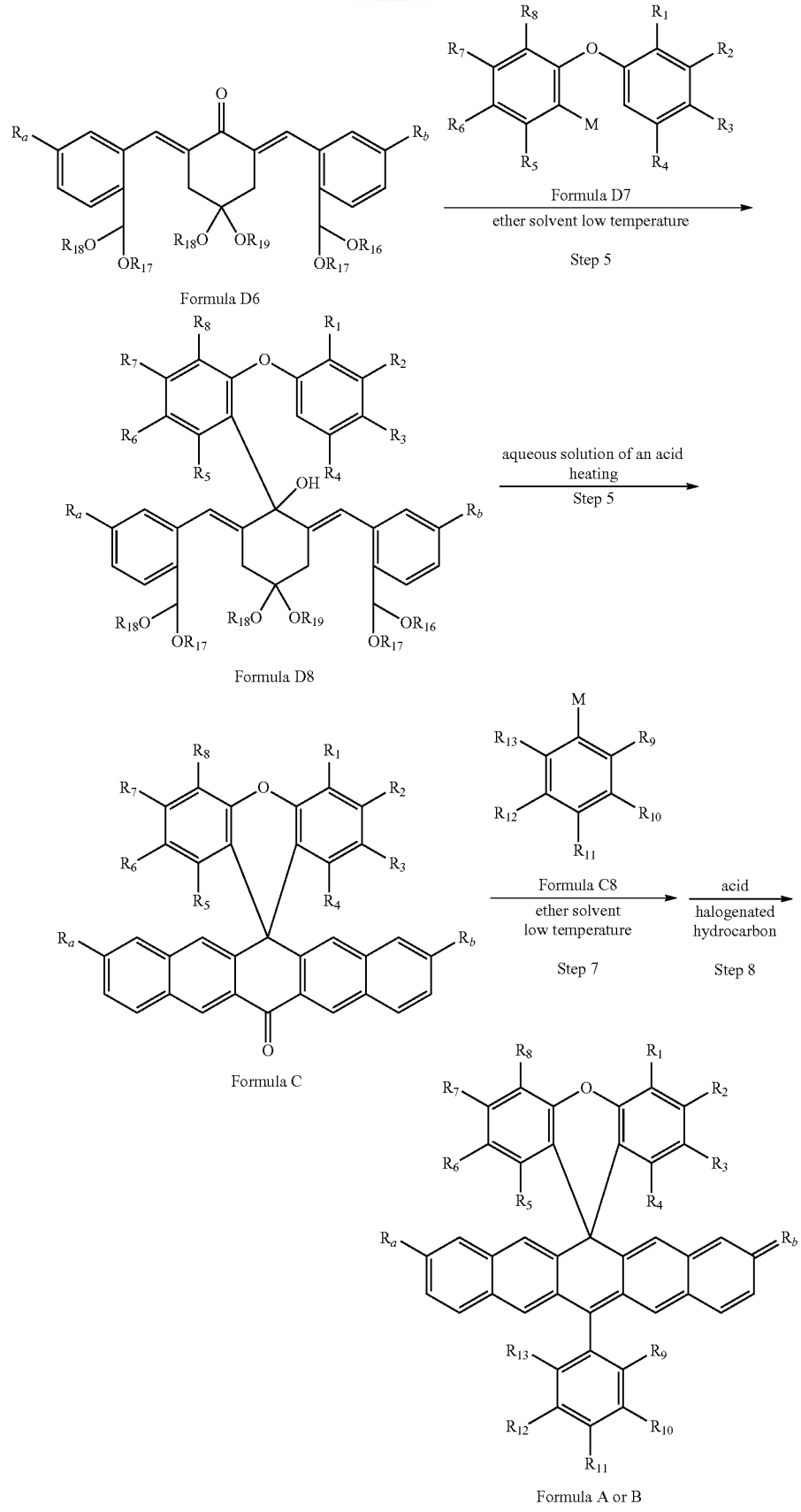

Step 1: Formylation of the para-position of $R_a$ group. The method used in the present disclosure is Vilseier-Haack formylation reaction. Solvent used in the reaction is halogenated hydrocarbon, such as dichloromethane, chloroform and 1,2-dichloroethane. If the reaction cannot take place at room temperature, the reactant mixture may be suitably heated to the boiling point of the selected solvent. $R_a$ may be $NR_{14}R_{15}$ or $OR_{14}$.

Step 2: Formation of acetal by an aldehyl group and alcohol under an acidic catalytic condition and a protection condition. A suitable alcohol includes methanol, ethanol, ethylene glycol, propanediol, 2,2-dimethyl propanediol, etc. Acid is a strong protonic acid, such as $H_2SO_4$, methylsulfonic acid and p-toluenesulfonic acid, etc. Solvent may be an alcohol necessary for forming acetal or some aromatic hydrocarbons with high boiling point. The common solvent is toluene. A water separator is required in this reaction to remove water in order to improve the reaction yield. $R_{16}$ and $R_{17}$ may be some simple alkyl groups, such as C1-C4 alkyl, or they may link together to form —$CH_2CH$—, —$CH_2CH_2CH_2$— or —$CH_2C(CH_3)_2CH_2$—, etc. Generally, the reaction is performed under 60-160° C., such as about 110° C.

Step 3: The reaction is first performed with a strong base (which may be a strong alkaline lithium reagent, a Grignard reagent, or an alkali metal) through a metal/halogen exchange reaction in an ether solvent at a low temperature, followed by quenching with a formylation reagent. The commonly used strong base is n-butyllithium or sec-butyllithium. The ether solvent generally is tetrahydrofuran, ethyl ether or dioxane. The temperature generally is −78° C. The formylation agent generally is DMF.

Step 4: A condensation reaction is performed in an aqueous solution of a base, such as concentrated NaOH or KOH. The concentration of the base is generally about 10% (mass percentage). $R_{18}$ and $R_{19}$ are selected from some simple alkyl groups, such as C1-4 alkyl, such as methyl and ethyl. $R_{18}$ and $R_{19}$ may link together to form —$CH_2CH$—, —$CH_2CH_2CH_2$— or —$CH_2C(CH_3)_2CH_2$—, etc. It should be understood that a mixture of compounds of Formula D6 with the same or different $R_a$ and $R_b$ may be produced by using a mixture of compounds of Formula D4 with the same or different IR. Generally, the reaction is performed at 10-60° C., such as about 40° C.

Step 5: An addition reaction is performed on the carbonyl of Formula D6 with Formula D7. In Formula D7, M is Li atom, $R_1$-$R_8$ are those as defined above. Step 5 is generally performed at a normal temperature, such as 15-35° C., preferably at room temperature. The ether solvent generally is tetrahydrofuran, ethyl ether or dioxane or a mixture thereof.

Step 6: Heating is performed in an aqueous solution of an acid. Generally a concentrated HCl is used. The temperature generally is 40-70° C., such as 60° C.

Step 7: An addition reaction between a compound of Formula C8 and a compound of Formula C is performed in an ether solvent at a low temperature (such as 30-60° C., preferably 35-45° C.). The ether solvent generally is ethyl ether, tetrahydrofuran, dioxane or a mixture thereof. In Formula C8, $R_9$-$R_{13}$ are those as defined above, M is Li or MgBr.

Step 8: The acid used in this step may be a protonic acid, such as HBr or HI, or Lewis acid, such as $BBr_3$ and $AlCl_3$, etc. According to the used acid, the solvent may be water, alcohol and halogenated hydrocarbon, etc.

The present disclosure will be illustrated by specific Examples. Unless otherwise indicated, the reagents and process conditions used in the Examples are conventional in the art.

EXAMPLE 1

Synthesis of Compounds 1a-1f

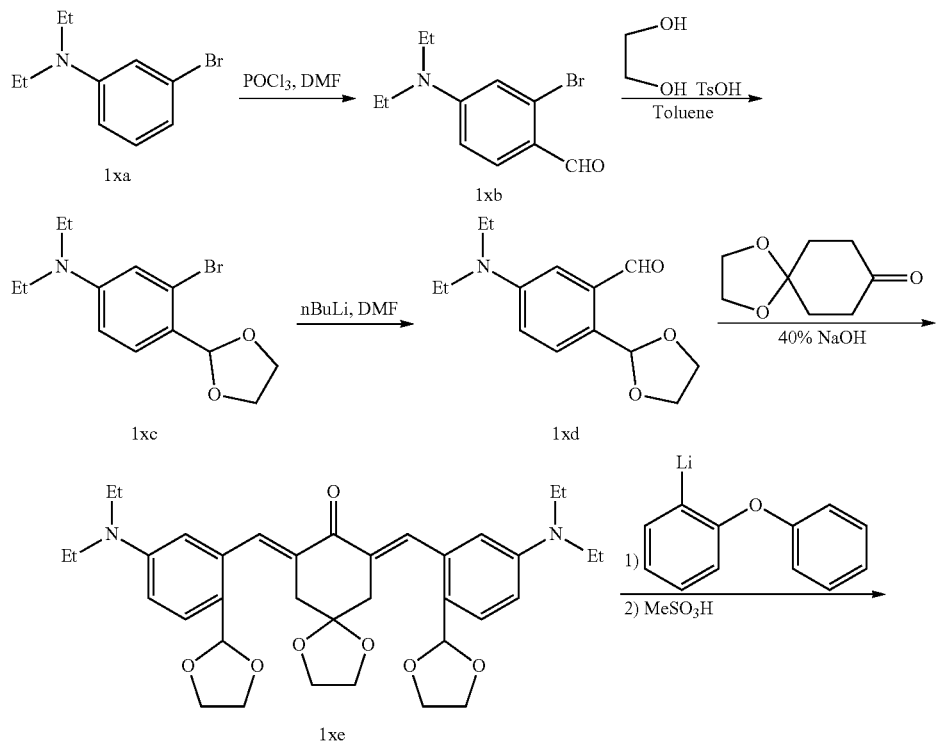

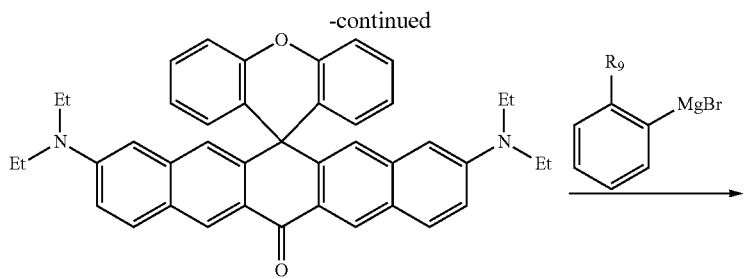

1xf

1xc

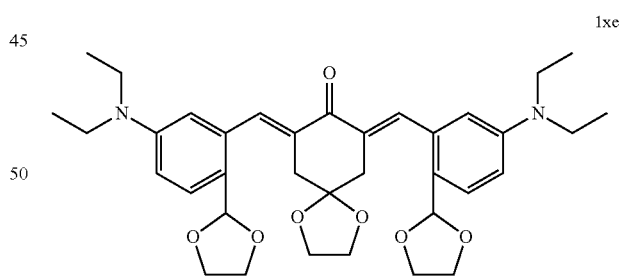

1a-1d 3 g (12 mmol) of compound 1xb, 1.5 g (24 mmol) of ethylene glycol and 0.2 g (1.2 mmol) of p-toluenesulfonic acid were added into a 100 ml single-neck round-bottom flask. 60 ml of toluene was added as a solvent. The flask was connected to a water separator and then heated with magnetic stirring to 140° C. for 6 hours. The solvent was removed under reduced pressure. The remaining reaction solution was treated with saturated $NaHCO_3$ solution and extracted with DCM. The organic phase was separated and dried over anhydrous $MgSO_4$ solid. The solvent was removed by rotary evaporator to give a thick brown oily liquid, which was isolated by column chromatography (PE:EA=20:1) to obtain a light yellow oily liquid, i.e., compound 1xc (2.84 g; yield 81%); $^1$H-NMR(CDCl$_3$, 400 MHz) δ 7.37 (d, J=8.8 Hz, 1H), 6.78 (d, J=4 Hz, 1H), 6.59 (dd, J=8.8 Hz, 2.4 Hz, 1H), 6.01 (s, 1H), 3.32 (q, J=7.2 Hz, 4H), 1.14 (t, J=6.8 Hz, 6H). $^{13}$C NMR (101 MHz, CDCl$_3$) δ 147.34, 126.59, 122.27, 120.27, 113.04, 108.69, 101.30, 63.38, 42.53, 10.54. HRMS (EI$^+$) Calculated ([M])$^+$, 299.0521; Found 299.0522.

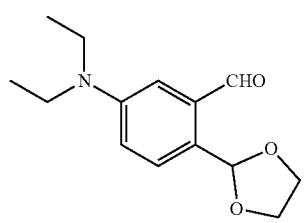

1xd 2.84 g (9.5 mmol) of compound 1xc and 50 ml of anhydrous tetrahydrofuran were added to a 100 ml round bottom flask. 6 ml (14.3 mmol, 2.5M) of n-butyllithium was added at −78° C. and under protection by argon. After reacting for 15 minutes, 1.47 ml (19 mmol) of dried DMF was added and the temperature was slowly raised to room temperature. The reaction was quenched by saturated NH$_4$Cl solution and the reaction solution was extracted with DCM and dried over anhydrous MgSO$_4$ solid. The solvent was removed by rotary evaporator to give a light yellow oily liquid, which was isolated by column chromatography (PE:EA=15:1) to obtain a yellow oily liquid, i.e., compound 1xd (2.12 g; yield 90%). $^1$H-NMR(CDCl$_3$, 400 MHz) δ 10.39 (s, 1H), 7.49 (d, J=8 Hz, 1H), 7.18 (d, J=2.8 Hz, 1H), 6.82 (dd, J=8.8 Hz, 2.8 Hz 1H), 6.22 (s, 1H), 4.17-4.04 (m, 4H), 3.40 (q, J=8 Hz, 4H), 3.17 (t, J=8 Hz, 6H). $^{13}$C NMR (101 MHz, CDCl$_3$)δ 192.61, 148.41, 135.53, 129.04, 124.88, 115.77, 111.96, 102.13, 65.13, 44.40, 12.43. HRMS (EI$^+$) Calculated ([M])$^+$, 249.1365; Found 249.1364.

1xe 1.48 g (6 mmol) of compound 1xd, 10 ml of ethanol and 0.463 g (3 mmol) of 4-cyclohexanedione monoethylene acetal were added into a 50 ml round bottom flask. 10 ml of 40% NaOH solution was dropped into the flask slowly. The solids in the reaction system were gradually increased. After half an hour, the reaction mixture was filtered to obtain a filter cake and then the filter cake was recrystalized with PE and EA to produce a fluffy bright yellow solid, i.e., compound 1xe (1.65 g; yield 92%). $^1$H-NMR(CDCl$_3$, 400 MHz) δ 8.13 (s, 2H), 7.41 (d, J=8.4 Hz, 2H), 6.63 (dd, J=8.8 Hz, 2.8 Hz, 2H), 6.42 (d, J=2.8 Hz, 2H), 5.78 (s, 2H), 4.15-3.94 (m, 8H), 3.85 (s, 4H), 3.35 (q, J=6.8 Hz, 8H), 2.92 (s, 4H), 1.15 (t, J=6.8 Hz, 12H). ¹³C NMR (101 MHz, CDCl₃) δ 188.00, 147.97, 139.42, 136.31, 133.73, 128.31, 122.28, 111.27, 107.06, 102.59, 65.27, 64.58, 44.45, 37.26, 12.59. HRMS (EI⁺), ([M⁺H])⁺ Calculated 618.3305; Found 618.3306.

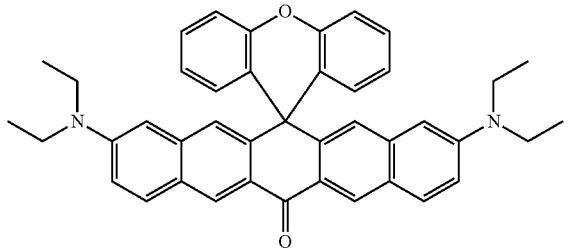

1xf

In a 100 ml round bottom flask were added 1.87 g (11 mmol) of diphenyl ether and 30 ml of dry THF. The flask was placed in an ice bath and 4.4 ml of n-butyllithium (c=2.5M) were added under protection of argon. After 2 hours of reaction, the whole reaction system was transferred to dry THF containing 1.36 g (2.2 mmol) of dissolved compound 1xe and reacted for 1 hour at room temperature. The reaction was then quenched with saturated NH₄Cl solution and extracted with DCM. The organic phase was separated and dried over anhydrous MgSO₄ solid. The solvent was removed by rotary evaporator to give a thick brown-red liquid which was separated by column chromatography (PE:EA=5:1) to give an orange-red solid, i.e., compound 1xf (0.58 g, yield 44%). ¹H-NMR(CDCl₃, 400 MHz) δ 8.85 (s, 2H), 7.84 (d, J=8 Hz, 2H), 7.27-7.25 (m, 2H), 7.17-7.12 (m, 4H), 7.03 (dd. J=9.2 Hz, 2.4 Hz, 2H), 6.77-6.70 (m, 4H), 6.51 (d, J=2 Hz, 2H), 3.38 (q, J=7.2 Hz, 8H), 1.14 (t, J=7.2 Hz, 12H). ¹³C NMR (101 MHz, CDCl₃) δ 183.65, 149.12, 147.99, 147.57, 138.49, 131.39, 131.09, 129.81, 128.61, 128.42, 127.50, 124.88, 124.43, 123.59, 116.34, 103.67, 46.07, 44.44, 12.77. HRMS (ES⁺) Calculated ([M+H])⁺, 603.3012; Found 603.3009.

MeOH 100/5) to give dye 1a, which was a purple solid (76 mg, 68%); ¹H-NMR(CDCl₃, 400 MHz) δ7.67-7.64 (m, 1H), 7.57-7.54 (m, 6H), 7.43-7.41 (m, 1H), 7.36-7.34 (m, 2H), 7.31-7.27 (m, 3H), 7.06-7.05 (m, 4H), 6.96-6.90 (m, 2H), 6.82 (dd, J=7.6 Hz, 1.2 Hz, 1H), 6.78 (dd, J=8 Hz, 1.2 Hz, 1H), 6.54 (s, 2H), 3.58 (q, J=7.2 Hz, 8H), 3.28 (s, 3H), 1.25 (t, J=7.2 Hz, 12H) HRMS (ES⁺) Calculated ([M+H])⁺, 677.3526; Found 677.3530.

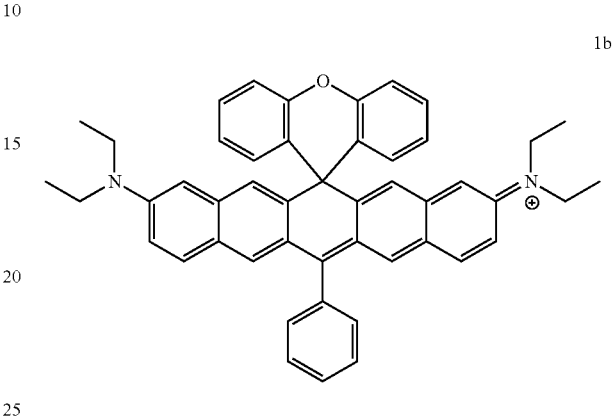

1b

O-methylphenyl Grignard reagent (2 mL, 2 mmol, 12 eq) was added to compound 1xf (100 mg, 0.17 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO₃ solution, extracted with dichloromethane, dried over anhydrous MgSO₄ solid and separated by column chromatography (silica gel, DCM/MeOH 100/5) to give dye 1b, which was a purple solid (72 mg, 65%); ¹H-NMR(CDCl₃, 400 MHz) δ7.77 (br, 3H), 7.71 (br, 2H), 7.60 (br, 4H), 7.35-7.26 (m, 4H), 7.05 (br, 4H), 6.96-6.92 (m, 2H), 6.84-6.82 (m, 2H), 6.53 (s, 2H), 3.57 (q, J=7.2 Hz, 8H), 1.26 (t, J=7.2 Hz, 12H) HRMS (ES⁺) Calculated ([M+H])⁺, 663.3370; Found 663.3371.

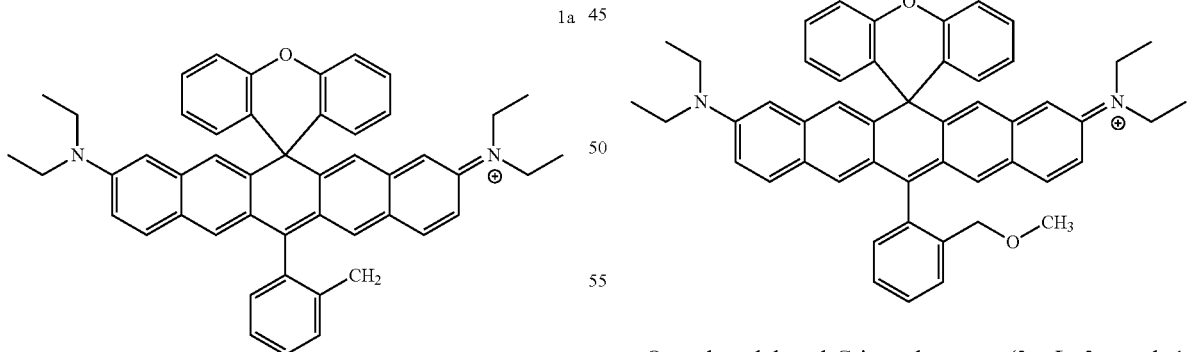

Phenyl Grignard reagents (2 mL, 2 mmol, 12 eq) was added to compound 1xf (100 mg, 0.17 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO₃ solution, extracted with dichloromethane, dried over anhydrous MgSO₄ and separated by column chromatography (silica gel, DCM/

O-methoxylphenyl Grignard reagent (2 mL, 2 mmol, 12 eq) was added to compound 1xf (100 mg, 0.17 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO₃ solution, extracted with dichloromethane, dried over anhydrous MgSO₄ solid and separated by column chromatography (silica gel, DCM/MeOH 100/5) to give dye 1c, which was a purple solid (85 mg, 73%); ¹H-NMR (CDCl₃, 400 MHz) δ7.79-7.73 (m, 2H), 7.70-7.66 (m, 1H), 7.37-7.29 (m, 4H) 7.08 (s, 2H), 7.06-7.03 (m, 4H), 6.98-6.81 (m, 4H), 4.40 (s, 2H), 3.57 (q, J=7.2 Hz, 8H), 3.15 (s, 3H), 1.26 (t, J=7.2 Hz, 12H) HRMS (ES⁺) Calculated ([M+H])⁺, 707.3632; Found 707.3638.

1d

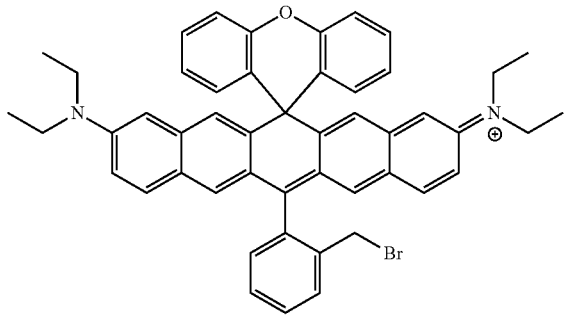

1c was dissolved in 1,2-dichloroethane. Excessive amount of BBr₃ were added and then the mixture was heated to 60° C. The reaction was quenched by water, separated, and subjected to column chromatography (silica gel, DCM/MeOH 100/5) to afford compound 1d, which was a purple solid with a yield of 92%. ¹H-NMR(CDCl₃, 400 MHz) δ 7.83-7.70 (m, 3H), 7.60-7.50 (m, 5H), 7.38-7.25 (m, 4H), 7.11-6.93 (m, 7H), 6.86-6.84 (m, 1H), 6.57-6.54 (m, 2H), 4.46 (s, 2H), 3.58 (t, J=7.2 Hz, 8H), 1.26 (q, J=7.2 Hz, 12H) HRMS (ES⁺) Calculated ([M+H])⁺; 757.2617 Found 757.2620.

1e

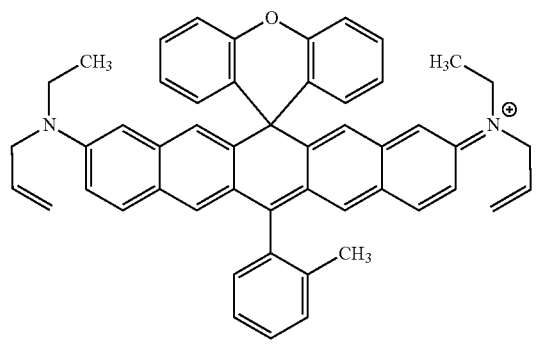

Compound 1e was synthesized by a similar method for synthesis of compound 1a.

1f

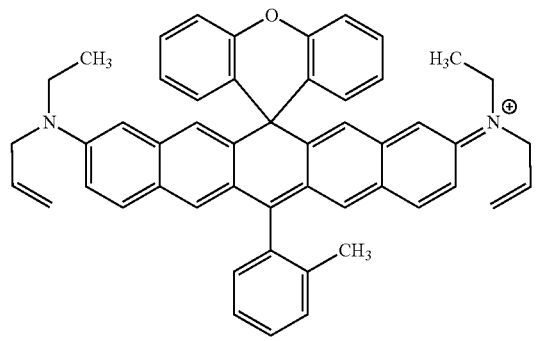

Compound 1f was synthesized by a similar method for synthesis of compound 1a. ¹H-NMR (CDCl₃, 400 MHz) δ7.67-7.54 (m, 6H), 7.43-7.29 (m, 6H), 7.08-7.05 (m, 4H), 6.97-6.90 (m, 2H), 6.81 (dd, J=7.2 Hz, 1.2 Hz, 1H), 6.77 (dd, J=7.6 Hz, 1.2 Hz, 1H), 6.56 (s, 2H), 5.88-5.78 (m, 1H), 5.20 (d, J=10.4 Hz, 2H), 5.08 (d, J=17.2 Hz, 2H), 4.15 (d, J=2.8 Hz, 4H), 3.59 (q, J=7.2 Hz, 4H), 2.28 (s, 3H), 1.26 (t, J=7.2 Hz, 6H).

EXAMPLE 2

Synthesis of Compounds 2a-2b

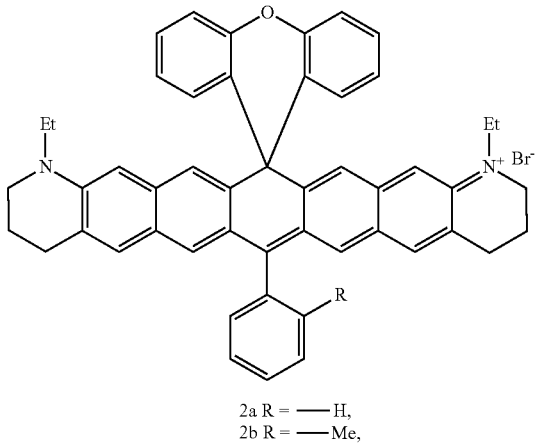

2a R = ——H,
2b R = ——Me,

Dye 1e (20 mg) was dissolved in 50% concentrated sulfuric acid (2 mL) under an ice bath and the resultant mixture was slowly warmed to room temperature and then kept for 2 hours. Copped ice (50 g) was added to the reaction system and then the reaction mixture was extracted with dichloromethane. After drying over magnesium sulfate, the dichloromethane in the organic phase was removed under reduced pressure, followed by purification by column chromatography to give dye 2a (17 mg), which was a purple solid.

Dye 1f (20 mg) was dissolved in 50% concentrated sulfuric acid (2 mL) under an ice bath and the resultant mixture was slowly warmed to room temperature and then kept for 2 hours. Copped ice (50 g) was added to the reaction system and then the reaction mixture was extracted with dichloromethane. After drying over magnesium sulfate, the dichloromethane in the organic phase was removed under reduced pressure, followed by purification by column chromatography to give dye 2b (14 mg), which was a purple solid.

EXAMPLE 3
Synthesis of Compounds 3a-3n
120 ml of DMF was added into a 250 ml single neck round bottom flask. 11 ml (119 mmol) of $POCl_3$ was added under an ice bath with magnetic stirring. Five minutes later,
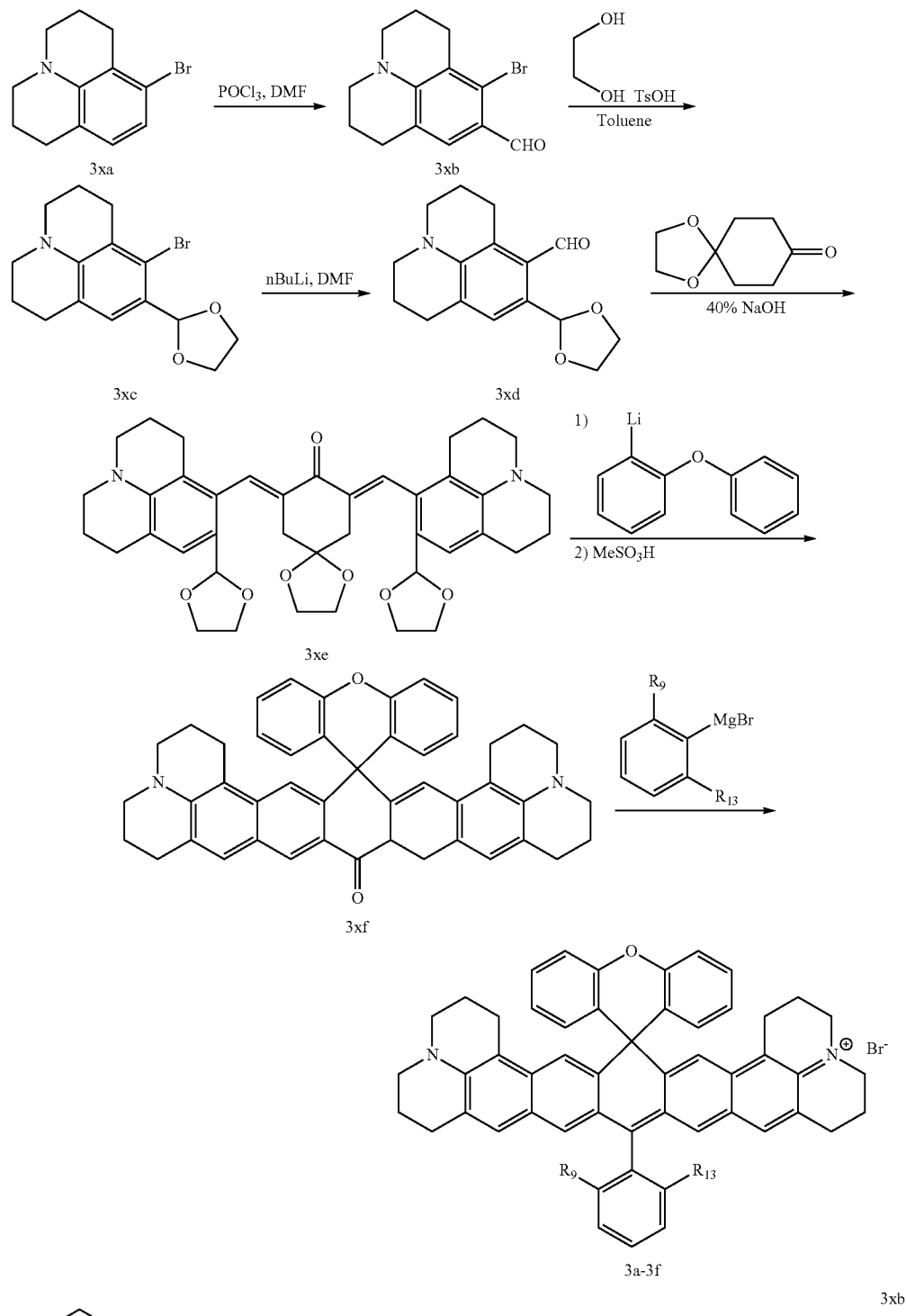
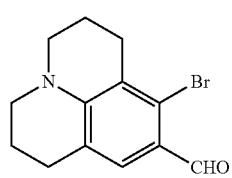
3xb the ice bath was removed. Reaction was continued at normal temperature for 30 minutes and then 20 g (79 mmol) of compound 3xa were added. The resultant mixture was heated to 80° C. and then reaction was carried out for 1 hour. The solvent was removed by rotary evaporator and the remaining reaction liquid was poured into an ice bath and left to stand for half an hour. 21.62 g of the solid compound 3xb was obtained as a yellow powder by filtration and drying under vacuum with a yield of 97%. $^1$H-NMR(CDCl$_3$, 400 MHz) δ1.90-1.98 (m, 4H), 2.69 (t, J=6.4 Hz, 2H), 2.82 (t, J=6.4 Hz, 2H), 3.24-3.30 (m, 4H), 7.40 (s, 1H), 10.08 (s, 1H). $^{13}$C-NMR (CDCl$_3$, 100 MHz) 21.07, 21.15, 27.44, 28.07, 49.81, 50.18, 119.24, 119.67, 121.42, 128.32, 129.56, 148.92, 190.92. HRMS (EI$^+$) Calculated ([M])$^+$, 279.0259; Found 279.0261.

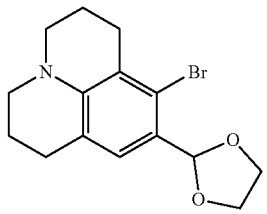

3xc 7 g (25 mmol) of compound 3xb, 2.3 g (37.5 mmol) of ethylene glycol and 0.43 g (2.5 mmol) of p-toluenesulfonic acid were added into a 250 ml single-neck round-bottom flask. 120 ml of toluene was added as a solvent. The round-bottom flask was connected to a water separator and then heated with magnetic stirring to 140° C. for 6 hours. The solvent was removed under reduced pressure. The remaining reaction solution was treated with saturated NaHCO$_3$ solution and extracted with DCM. The organic phase was separated and dried over anhydrous MgSO$_4$ solid. The solvent was removed by rotary evaporator to give a thick brownish black oily liquid, which was isolated by column chromatography (PE:EA=20:1) to obtain a light yellow oily liquid, i.e., compound 3xc (6.18 g; yield 75%). $^1$H-NMR(CDCl$_3$, 400 MHz) δ 1.92-1.98 (m, 4H), 2.70-2.73 (t, J=6.4 Hz, 2H), 2.80 (t, J=6.4 Hz, 2H), 3.10-3.16 (m, 4H), 4.00-4.15 (m, 4H), 6.07 (s, 1H), 7.04 (s, H). $^{13}$C-NMR (CDCl$_3$, 100 MHz) δ 21.88, 21.92, 27.66, 28.81, 49.51, 49.96, 85.24, 103.61, 120.43, 120.58, 122.92, 123.68, 125.54, 145.18. HRMS (EI$^+$) Calculated ([M])$^+$, 323.0521; Found 323.0518.

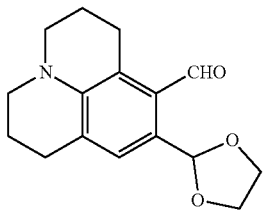

3xd 5 g (15.4 mmol) of compound 3xc and 100 ml of anhydrous tetrahydrofuran were added to a 250 ml round bottom flask. 11 ml (18.5 mmol, 1.6M) of n-butyllithium was added at −78° C. and under protection by argon. After reacting for 15 minutes, 1.35 ml (18.5 mmol) of dried DMF was added and the temperature was slowly raised to room temperature. The reaction was quenched by saturated NH$_4$Cl solution and the reaction solution was extracted with DCM and dried over anhydrous MgSO$_4$ solid. The solvent was removed by rotary evaporator to give a light yellow oily liquid, which was isolated by column chromatography (PE:EA=15:1) to obtain a yellow oily liquid. i.e., compound 3xd (4.13 g; yield 97%).

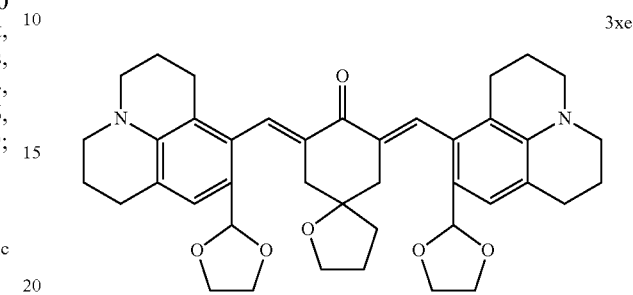

3xe 3 g (11 mmol) of compound 3xd, 10 ml of ethanol and 0.858 g (5.5 mmol) of 4-cyclohexanedione monoethylene acetal were added into a 100 ml single-neck round-bottom flask. 10 ml of 40% NaOH solution were dropped into the flask slowly. The solids in the reaction system were gradually increased. After half an hour, the reaction mixture was filtered to obtain a filter cake and then the filter cake was recrystalized with PE and EA to produce a fluffy bright yellow solid, i.e., compound 3xe (3.5 g; yield 95%). $^1$H-NMR(CDCl$_3$, 400 MHz) δ 1.90-1.97 (m, 8H), 2.46-2.52 (t, 6H), 2.68-2.77 (t, 6H), 3.11-3.15 (m, 8H), 3.81 (m, 4H), 3.90 (s, 4H), 4.08 (m, 4H), 5.60 (s, 2H), 7.01 (s, 2H), 7.79 (s, 2H). $^{13}$C-NMR (CDCl$_3$, 100 MHz) δ 21.91, 25.36, 27.81, 37.01, 49.70, 50.24, 64.47, 64.54, 64.66, 65.04, 65.19, 102.61, 107.11, 118.28, 121.03, 126.06, 133.09, 135.60, 139.36, 139.36, 143.81. HRMS (ES$^+$) Calculated ([M+H])$^+$, 667.3383; Found 667.3388.

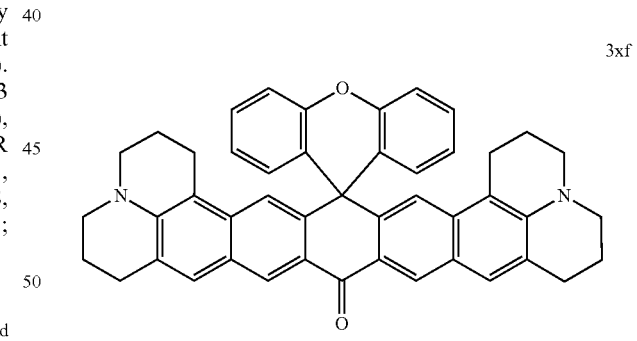

3xf

In a 100 ml round bottom flask were added 1 g (59 mmol) of diphenyl ether and 30 ml of dry THF. The flask was placed in an ice bath and 5.5 ml of n-butyllithium (c=1.6M) was added under protection of argon. After 2 hours of reaction, the whole reaction system was transferred to dry THF containing 1 g (1.5 mmol) of dissolved compound 3xe and reacted for 1 hour at normal temperature. The reaction was quenched with saturated NH$_4$Cl solution and extracted with DCM. The organic phase was separated and dried over anhydrous MgSO$_4$ solid. The solvent was removed by rotary evaporator to give a thick brown-red liquid which was separated by column chromatography (PE:EA=5:1) to give an orange-red solid, i.e., compound 3xf (0.66 g, 15 mmol), with a yield of 67%. $^1$H-NMR(CDCl$_3$, 400 MHz) δ 1.87-

1.98 (m, 8H), 2.61 (t, J=6.4 Hz, 4H), 2.88 (t, J=6.4 Hz, 4H), 3.14 (t, J=5.6 Hz, 4H), 3.21 (t, J=5.6 Hz, 4H), 6.68-6.73 (m, 4H), 7.09-7.13 (m, 2H), 7.21-7.23 (d, J=8 Hz, 4H), 7.45 (s, 2H), 8.72 (s, 2H). $^{13}$C-NMR (CDCl$_3$, 100 MHz) δ 0, 20.28, 20.81, 21.95, 27.70, 45.56, 48.71, 49.50, 108.49, 115.16, 122.32, 122.91, 123.62, 123.74, 125.28, 126.14, 126.33, 126.97, 129.29, 130.17, 134.13, 142.42, 146.07. HRMS (ES$^+$) Calculated ([M+H])$^+$, 651.3013; Found 651.3014.

3a

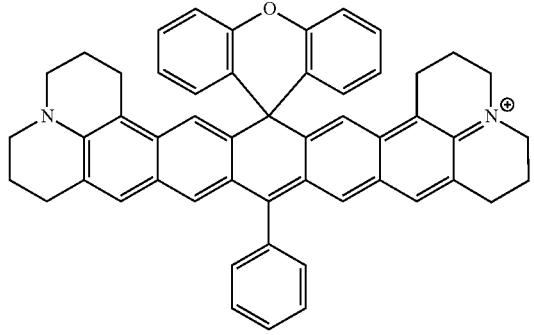

Phenyl Grignard reagents (2 mL, 2 mmol, 13 eq) were added to compound 3xf (100 mg, 0.15 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO$_3$ solution, extracted with dichloromethane, dried over anhydrous MgSO$_4$ solid and separated by column chromatography (DCM/MeOH) to give dye 3a, which was a purple solid (79 mg, 72%). $^1$H-NMR(CDCl$_3$, 400 MHz) δ 1.94 (m, 8H), 2.57 (t, J=5.6 Hz, 4H), 2.76 (t, J=5.6 Hz, 4H), 3.46 (t, J=5.6 Hz, 4H), 3.52 (t, J=5.6 Hz, 4H), 6.86 (d, J=8 Hz, 2H), 6.90 (t, J=7.2 Hz, 2H), 7.10 (s, 2H), 7.14 (s, 2H), 7.23-7.30 (m, 4H), 7.47 (s, 2H), 7.54 (m, 2H), 7.70 (m, 3H). $^{13}$C NMR (101 MHz, CDCl$_3$) δ 162.11, 149.56, 148.89, 147.24, 137.92, 136.12, 135.80, 130.87, 130.11, 129.92, 129.63, 129.54, 128.66, 128.50, 126.97, 126.08, 125.97, 125.77, 123.97, 117.05, 113.80, 80.17, 77.45, 77.13, 76.81, 51.80, 50.83, 48.10, 28.05, 22.48, 20.94, 20.36. HRMS (ESI) Calculated ([M])$^+$, 711.3375; Found 711.3370.

3b

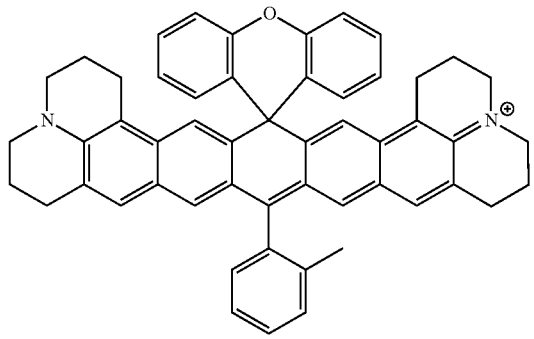

O-methylphenyl Grignard reagents (2 mL, 2 mmol 13 eq) were added to compound 3xf (100 mg, 0.15 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO$_3$ solution, extracted with dichloromethane, dried over anhydrous MgSO$_4$ solid and separated by column chromatography (silica gel, DCM/MeOH 100/5) to give dye 3b, which was a purple solid (76 mg, 68%). $^1$H-NMR(CDCl$_3$, 400 MHz) δ 1.92 (m, 8H), 2.22 (s, 3H), 2.55 (t, J=5 Hz, 4H), 2.74 (t, J=6 Hz, 4H), 3.44 (t, J=5.6 Hz, 4H), 3.51 (t, J=5.6 Hz, 4H), 6.77-6.91 (m, 4H), 7.07 (s, 2H), 7.14 (s, 2H), 7.21-7.29 (m, 4H), 7.31 (s, 2H), 7.36 (d, J=8 Hz, 1H), 7.46-7.50 (m, 2H), 7.57 (t, J=8 Hz, 1H). $^{13}$C NMR (126 MHz, CDCl$_3$) δ 161.99, 149.52, 148.83, 147.24, 136.88, 136.20, 135.46, 130.76, 130.62, 129.85, 129.78, 129.68, 129.50, 128.42, 126.99, 126.04, 125.99, 125.95, 125.63, 123.94, 123.89, 117.03, 117.00, 113.86, 51.77, 50.80, 47.94, 27.97, 22.44, 20.88, 20.30, 19.76. HRMS (ESI$^+$) Calculated ([M])$^+$, 725.3526; Found 725.3531.

3c

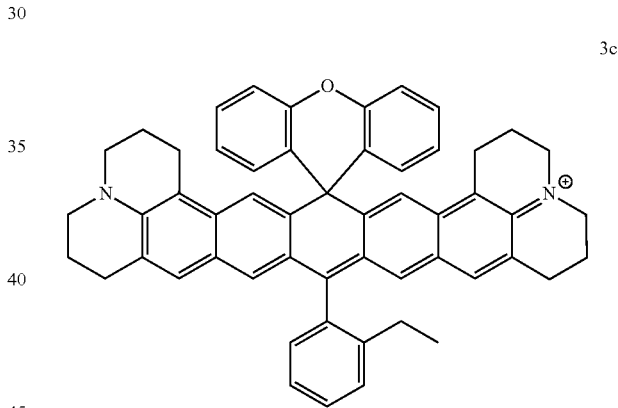

O-ethylphenyl Grignard reagents (2 mL, 2 mmol 13 eq) were added to compound 3xf (100 mg, 0.15 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO$_3$ solution, extracted with dichloromethane, dried over anhydrous MgSO$_4$ solid and separated by column chromatography (DCM/MeOH) to give dye 3c, which was a purple solid (70 mg, 61%). $^1$H-NMR(CDCl$_3$, 400 MHz) δ1.11 (t, J=8 Hz, 3H), 1.93 (m, 8H), 2.53-2.59 (m, 6H), 2.74 (t, J=6 Hz, 4H), 3.44 (t, J=5.6 Hz, 4H), 3.51 (t, J=5.6 Hz, 4H), 6.79 (d, J=8 Hz, 1H), 6.84 (t, J=8 Hz, 2H), 6.91 (t, J=8 Hz, 1H), 7.08 (s, 2H), 7.14 (s, 2H), 7.20-7.33 (m, 5H), 7.35 (s, 2H), 7.48 (t, J=8 Hz, 1H), 7.56 (d, J=8 Hz, 1H), 7.62 (t, =8 Hz, 1H). $^{13}$C NMR (101 MHz, CDCl$_3$) δ 161.99, 149.58, 149.08, 148.76, 147.24, 142.53, 137.20, 136.26, 134.88, 130.82, 130.08, 129.96, 129.80, 129.67, 128.98, 128.57, 128.47, 127.06, 126.13, 126.06, 126.00, 125.90, 124.03, 123.92, 117.19, 117.04, 113.95, 51.84, 50.87, 48.03, 28.05, 26.70, 22.52, 20.95, 20.37, 15.42. HRMS (ESI) Calculated ([M])$^+$, 739.3688; Found 739.3685.

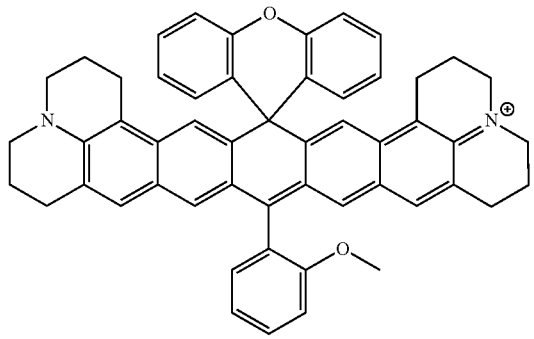

3d

O-methoxyphenyl Grignard reagents (2 mL, 2 mmol, 13 eq) were added to compound 3xf (100 mg, 0.15 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO₃ solution, extracted with dichloromethane, dried over anhydrous MgSO₄ solid and separated by column chromatography (DCM/MeOH) to give dye 3d, which was a purple solid (77 mg, 67%).
$^1$H-NMR(CDCl$_3$+CD$_3$OD, 400 MHz) δ 1.86-1.92 (m, 8H), 2.43-2.67 (m, 4H), 2.74 (t, J=6 Hz, 4H), 3.37 (t, J=5.6 Hz, 4H), 3.44 (t, J=5.6 Hz, 4H), 3.83 (s, 3 Hz, 4H), 6.88 (d, J=8 Hz, 1H), 6.92 (d, J=8 Hz, 1H), 6.69-7.00 (m, 1H), 7.11 (s, 2H), 7.15 (s, 2H), 7.18-7.26 (m, 2H), 7.30-7.34 (m, 3H), 7.38 (d, J=8 Hz, 2H), 7.46 (d, J=8 Hz, 1H), 7.50 (s, 2H), 7.72 (t, 0.18 Hz, 1H). $^{13}$C NMR (101 MHz, CDCl$_3$) δ 161.02, 157.16, 149.95, 149.39, 147.97, 147.28, 137.47, 136.27, 131.31, 131.07, 130.86, 130.74, 129.68, 129.44, 128.75, 128.69, 128.17, 77.50, 77.19, 76.87, 56.08, 51.71, 50.74, 48.22, 28.04, 22.49, 20.95, 20.37. HRMS (ESI⁺) Calculated ([M])⁺, 741.3476; Found 741.3477.

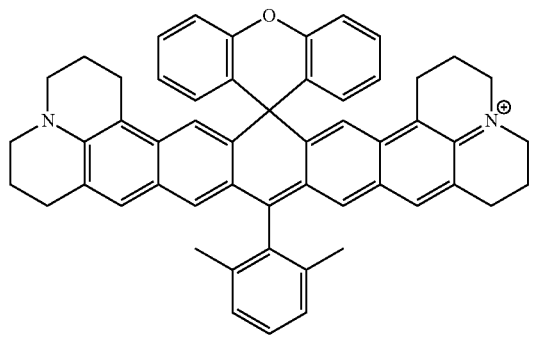

3e 2,6-Dimethylphenyl Grignard reagents (2 mL, 2 mmol, 13 eq) were added to compound 3xf (100 mg, 0.15 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO₃ solution, extracted with dichloromethane, dried over anhydrous MgSO₄ solid and separated by column chromatography (DCM/MeOH) to give dye 3e, which was a purple solid (68 mg, 60%). $^1$H-NMR(CDCl$_3$, 400 MHz) δ1.84-1.90 (m, 8H), 2.48-2.51 (m, 4H), 2.51 (s, 6H), 2.72 (t, J=6 Hz, 4H), 3.35 (t, J=5.6 Hz, 4H), 3.43 (t, J=5.6 Hz, 4H), 6.87 (d, J=8 Hz, 2H), 6.93 (t, J=8 Hz, 2H), 7.17 (d, J=8 Hz, 4H), 7.24 (s, 2H), 7.27 (d, J=8 Hz, 2H), 7.32 (d, J=8 Hz, 2H), 7.38 (s, 1H), 7.67 (s, 2H). $^{13}$C NMR (101 MHz, CDCl$_3$) δ 163.11, 149.48, 148.89, 147.33, 138.22, 138.15, 136.19, 135.73, 131.19, 130.85, 129.94, 129.59, 128.48, 127.80, 126.91, 126.01, 125.72, 123.96, 117.05, 113.72, 77.38, 77.27, 77.06, 76.75, 51.77, 50.80, 48.06, 28.07, 22.49, 21.52, 20.97, 20.38. HRMS (ESI⁺) Calculated ([M])⁺, 739.3688; Found 739.3683.

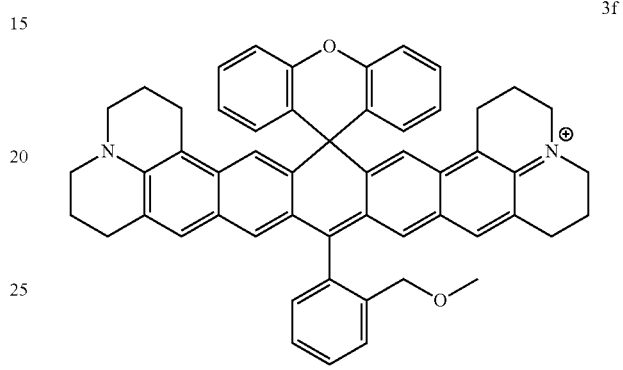

3f

O-(methoxy)methylphenyl Grignard reagents (2 mL, 2 mmol, 13 eq) were added to compound 3xf (100 mg, 0.15 mmol) in THF in an ice bath. Reaction was performed at 40° C. for 2 hours. 5 ml of methyl sulfonic acid was added into the reaction system and the mixture was stirred at room temperature for half an hour, neutralized with saturated NaHCO₃ solution, extracted with dichloromethane, dried over anhydrous MgSO₄ solid and separated by column chromatography (silica gel, DCM/MeOH 100/5) to give dye 3f, which was a purple solid (75 mg, 64%). $^1$H-NMR (CDCl$_3$, 400 MHz) δ7.15-7.62 (m, 3H), 7.43-7.20 (m, 7H), 7.16 (s, 2H) 7.08 (s, 2H), 6.90-6.87 (m, 4H), 4.37 (s, 2H), 3.53-3.46 (m, 8H), 3.18 (s, 3H), 2.75 (s, 4H), 2.68 (s, 4H), 1.94 (s, 8H); $^{13}$C NMR (101 MHz, CDCl$_3$) δ 149.58, 149.10, 148.62, 147.20, 137.12, 136.21, 130.83, 130.13, 129.75, 128.99, 128.56, 128.43, 127.99, 127.02, 126.09, 125.82, 124.02, 123.91, 117.15, 116.99, 113.92, 77.50, 77.39, 77.18, 76.86, 72.65, 58.55, 51.83, 50.86, 47.99, 28.03, 22.50, 20.93, 20.34. HRMS (ESI⁺) Calculated ([M])⁺, 755.3638; Found 755.3638.

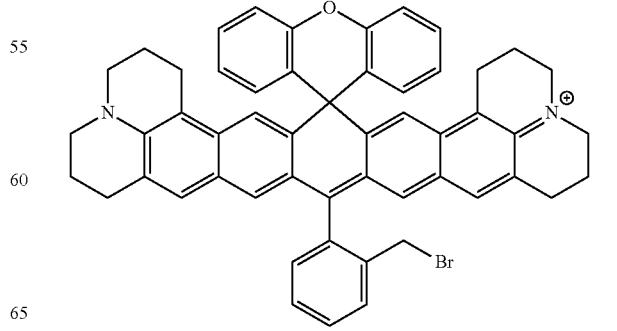

3g 50 mg (0.066 mmol) of compound 3f was dissolved in 30 ml of 1,2-dichloroethane. 0.5 ml of boron tribromide was added at room temperature, and the mixture was stirred at room temperature for 1 hour. The excessive boron tribromide was quenched by adding water. Then the mixture was neutralized with saturated NaHCO$_3$ solution, extracted with dichloromethane, dried over anhydrous magnesium sulfate and purified by column chromatography (DCM/MeOH 100/2) to give compound 3g, which was a purple solid (45 mg, 84%); $^1$H NMR (400 MHz, CDCl$_3$) δ 7.78 (d, J=8 Hz, 1H), 7.71 (t, J=8 Hz, 1H), 7.66 (d, J=8 Hz, 1H), 7.46 (d, J=8 Hz, 1H), 7.34-7.30 (m, 4H), 7.25 (dd, J=8 Hz, 2.4 Hz, 1H), 7.22 (dd, J=8 Hz, 2.4 Hz, 1H), 7.16 (s, 2H), 7.09 (s, 2H), 6.96-6.92 (m, 2H), 6.90 (dd, J=8 Hz, 2.4 Hz, 1H), 6.88 (d, J=8 Hz, 1H), 4.43 (s, 2H), 3.52-3.44 (m, 8H), 2.77-2.74 (m, 4H), 2.69-2.66 (m, 4H), 1.96-1.92 (m, 8H); $^{13}$C NMR (101 MHz, CDCl$_3$) δ 7.78, 7.76, 7.73, 7.71, 7.69, 7.67, 7.65, 7.63, 7.46, 7.44, 7.34, 7.32, 7.32, 7.30, 7.28, 7.25, 7.24, 7.23, 7.22, 7.21, 7.20, 7.16, 7.09, 6.96, 6.94, 6.92, 6.90, 6.90, 6.88, 4.43, 3.52, 3.45, 3.44, 2.77, 2.75, 2.74, 2.59, 2.57, 2.56, 1.95, 1.94, 1.92, 0.00. HRMS (ESI) Calculated ([M]$^+$, 803.2637; Found 803.2636.

3h

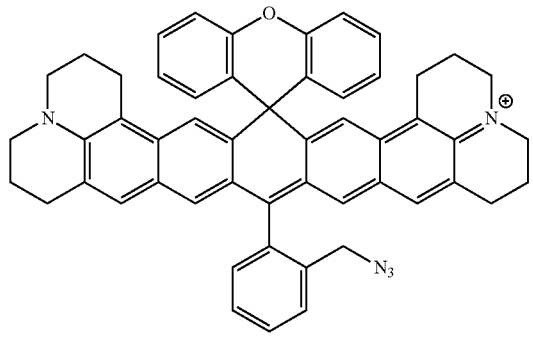

Compound 3g (50 mg, 0.062 mmol) and NaN$_3$ (4 mg, 0.062 mmol, 1 eq) were dissolved in 20 ml isopropanol. The resultant mixture was stirred for half an hour at room temperature. The mixture was treated with water, extracted with dichloromethane, dried over anhydrous magnesium sulfate and purified by column chromatography (DCM/MeOH 100/2) to give compound 3h, which was a purple solid (35 mg, 73%); $^1$H NMR (400 MHz, CDCl$_3$) δ 7.77-7.68 (m, 3H), 7.61 (d, J=8 Hz), 7.33-7.23 (m, 6H), 7.16 (s, 2H), 7.09 (s, 2H), 6.94-6.90 (m, 2H), 6.86-6.84 (m, 2H), 4.29 (s, 2H), 3.53 (s, 4H), 3.46 (s, 3.46), 2.76-2.75 (m, 4H), 2.59-2.56 (m, 4H), 1.96-1.93 (8H); $^{13}$C NMR (101 MHz, CDCl$_3$) δ 149.70, 149.06, 130.96, 130.92, 130.10, 130.05, 129.84, 128.92, 128.61, 128.52, 127.14, 126.30, 126.05, 124.11, 124.07, 117.14, 117.06, 114.25, 52.85, 51.89, 50.92, 28.02, 22.52, 20.93, 20.36.

3i

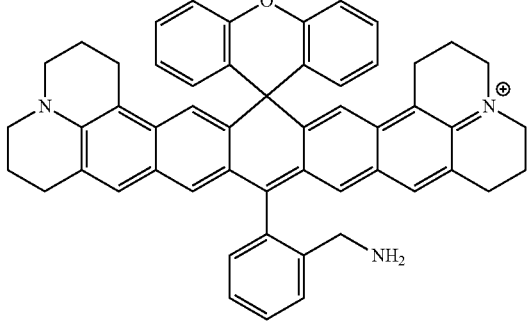

Compound 3g (50 mg, 0.062 mmol) was dissolved in 20 ml methanol saturated with ammonia. The resultant mixture was stirred for half an hour at room temperature, treated with water, extracted with dichloromethane, dried over anhydrous magnesium sulfate and purified by column chromatography (DCM/MeOH 100/2) to afford compound 3i, which was a purple solid (31 mg, 63%); $^1$H NMR (40 MHz, CDCl$_3$) δ 7.51 (d, J=8.0 Hz, 1H), 7.38 (t, J=8.0 Hz, 1H), 7.29 (s, 2H), 7.28-7.14 (m, 4H), 7.13 (s, 2H), 7.02 (s, 2H), 7.08 (dd, J=8.0 Hz, 1.6 Hz, 1H), 6.94 (d, J=8.0 Hz, 1H), 6.79 (t, J=8.0 Hz, 1H), 6.75 (t, J=8.0 Hz, 1H), 6.72 (dd, J=8.0 Hz, 1.6 Hz, 1H), 4.68 (s, 2H), 3.10-3.04 (m, 8H), 2.77 (t, J=8.0 Hz, 4H), 2.68-2.52 (m, 4H), 1.93-1.88 (m, 8H); $^{13}$C NMR (101 MHz, CDCl$_3$) δ 151.5, 149.9, 148.1, 142.8, 141.8, 141.3, 134.9, 133.1, 132.3, 131.8, 131.7, 127.9, 127.1, 126.9, 126.7, 126.0, 125.9, 125.1, 124.9, 124.8, 123.4, 123.2, 121.8, 116.1, 115.7, 109.9, 70.9, 52.1, 50.5, 49.9, 47.2, 28.6, 23.0, 22.2, 21.7. HRMS (ESI$^+$) Calculated C$_{53}$H$_{46}$N$_3$O ([M+H])$^+$, 740.3641; Found 740.3641.

3j

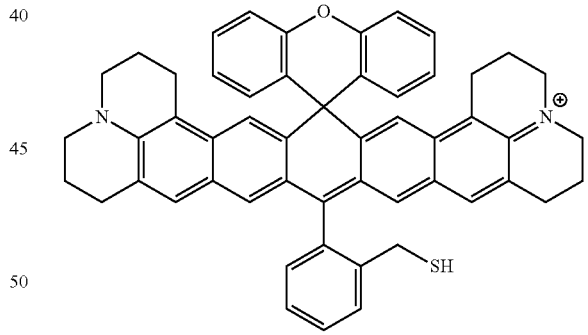

Compound 3d (50 mg, 0.062 mmol) and Na$_2$S.9H$_2$O (13 mg, 0.062 mmol, 1 eq) were dissolved in 20 ml isopropanol and the resultant mixture was stirred at room temperature for half an hour. The mixture was treated with water, extracted with dichloromethane, dried over anhydrous magnesium sulfate and purified by column chromatography (DCM/MeOH 100/2) to afford compound 3j, which was a purple solid (42 mg, 85%). $^1$H NMR (40 MHz, CDCl$_3$) δ 7.53 (d, J=8.0 Hz, 1H), 7.35 (t, J=8.0 Hz, 1H), 7.29 (s, 2H), 7.28-7.12 (m, 5H), 7.08 (dd, J=8.0 Hz, 1.2 Hz, 1H), 7.05 (s, 2H), 6.95 (d, J=8.0 Hz, 1H), 6.81 (t, J=8.0 Hz, 1H), 6.75 (t, J=8.0 Hz, 1H), 6.67 (dd, J=8.0 Hz, 1.6 Hz, 1H), 4.74 (s, 2H), 3.07 (t, J=8.0 Hz, 4H), 3.03 (t, J=8.0 Hz, 4H), 2.75 (t, J=8.0 Hz, 4H), 2.68-2.50 (m, 4H), 1.92-1.87 (m, 8H); $^{13}$C NMR (101

MHz, CDCl₃) δ 152.3, 149.9, 148.1, 142.1, 141.3, 141.2, 135.3, 133.4, 132.3, 132.2, 131.8, 131.5, 128.5, 127.9, 127.3, 127.1, 126.9, 126.8, 126.1, 124.9, 124.5, 124.3, 123.6, 123.2, 116.2, 115.7, 109.8, 77.4, 77.0, 76.7, 66.5, 50.5, 49.9, 47.2, 38.8, 28.6, 23.0, 22.2, 21.7. HRMS (ESI) Calculated C₅₃H₄₅N₂OS ([M+H])⁺, 757.3253; Found 757.3253.

142.52, 138.37, 137.32, 132.13, 131.16, 131.03, 130.69, 130.46, 130.05, 129.96, 129.09, 128.74, 128.02, 127.81, 127.46, 127.41, 126.96, 125.53, 118.40, 118.14, 115.02, 112.25, 79.51, 57.19, 52.64, 51.62, 49.45, 49.23, 49.02, 48.81, 48.60, 28.92, 23.49, 21.94, 21.40. MS (ESI−) Calculated ([M])−, 978.2; Found 489.1.

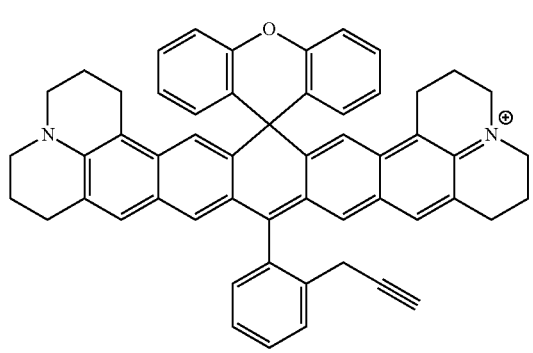

3k

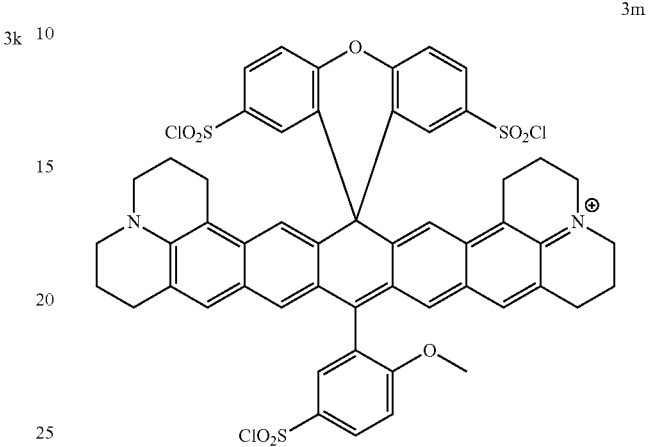

3m

Compound 3g (50 mg, 0.062 mmol) and LiCCH (4 mg, 0.062 mmol, 1 eq) were dissolved in 20 ml of isopropanol and the resultant mixture was stirred for half an hour at room temperature. The mixture was treated with water, extracted with dichloromethane, dried over anhydrous magnesium sulfate and purified by column chromatography (DCM/MeOH 100/2) to afford compound 3k as a purple solid (38 mg, 86%).

Compound 3d (50 mg, 0.067 mmol) was dissolved in trifluoromethanesulfonic anhydride and 1 ml of chlorosulfonic acid was added in an ice bath. The mixture was kept in the ice bath for half an hour and then neutralized with saturated NaHCO₃ solution, extracted with DCM, dried over anhydrous magnesium sulfate, and purified by column chromatography [silica gel, DCM/MeOH 100/2] to afford compound 3m as a purple solid (48 mg, 68%); 1H-NMR (CD3OD+CDCl3, 500 MHz) δ 8.38 (dd, J=8 Hz, 2.4 Hz, 1H), 8.14 (d, J=2.4 Hz, 1H), 8.11 (dd, J=8 Hz, 2.4 Hz, 1H), 7.92 (dd, J=8 Hz, 2.4 Hz, 1H), 7.79 (d, J=8 Hz, 1H), 7.76 (d, J=2.4 Hz, 1H), 7.66 (d, J=2.4 Hz, 1H), 7.62 (d, J=8 Hz, 1H), 7.49 (d, J=8 Hz, 1H), 7.34 (s, 2H), 7.18 (s, 2H), 6.95 (s, 2H), 4.03 (s, 3H), 3.52-3.47 (m, 8H), 2.81-2.78 (m, 4H), 2.53-2.49 (m, 4H), 2.0-1.9 (m, 8H); 13C NMR (101 MHz, CDCl3); HRMS (ESI+) Calculated ([M])+, 1035.1169; Found 1035.1167.

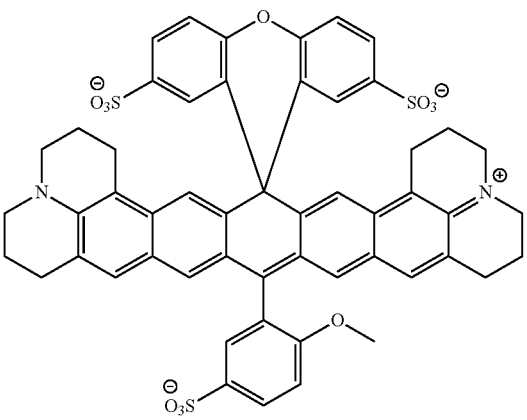

3l

Compound 3d (50 mg, 0.067 mmol) was dissolved in concentrated sulfuric acid. The resultant mixture was stirred overnight at room temperature, neutralized with saturated NaHCO₃ solution, and purified by column chromatography [reverse silica gel, H₂O/MeOH 100/20] to give compound 3l as a purple solid (45 mg, 64%); 1H-NMR(CD3OD+CDCl₃, 500 MHz) δ1.86 (m, 8H), 2.60 (m, 4H), 2.69 (t, J=7 Hz, 4H), 3.33 (t, J=5.5 Hz, 4H), 3.40 (t, J=5.5 Hz, 4H), 3.94 (s, 3H), 7.10 (s, 2H) 7.17 (s, 2H), 7.39 (t, J=8 Hz, 1H), 7.41 (d, J=8 Hz, 1H), 7.42 (d, J=2 Hz, 1H), 7.47 (d, J=8 Hz, 1H), 7.51 (d, J=8 Hz, 1H), 7.52 (s, 2H), 7.72 (dd, J=8 Hz, 2 Hz, 1H), 7.79 (dd, J=8 Hz, 2 Hz, 1H), 7.94 (d, J=2 Hz, 1H), 8.16 (dd, J=8 Hz, 2 Hz, 2H). 13C NMR (101 MHz, MeOD) δ 160.69, 160.54, 151.56, 150.86, 149.84, 148.25, 142.80, 3n Compound 3d (50 mg, 0.062 mmol) and NBS (35 mg, excessive) were dissolved in 20 ml of isopropanol in an ice bath and the resultant mixture was stirred for half an hour at room temperature. The mixture was treated with water, extracted with dichloromethane, dried over anhydrous magnesium sulfate and purified by column chromatography (DCM/MeOH 100/2) to afford compound 3n as a purple solid (63 mg, 87%).

EXAMPLE 4

Synthesis of Compounds 4a-4c

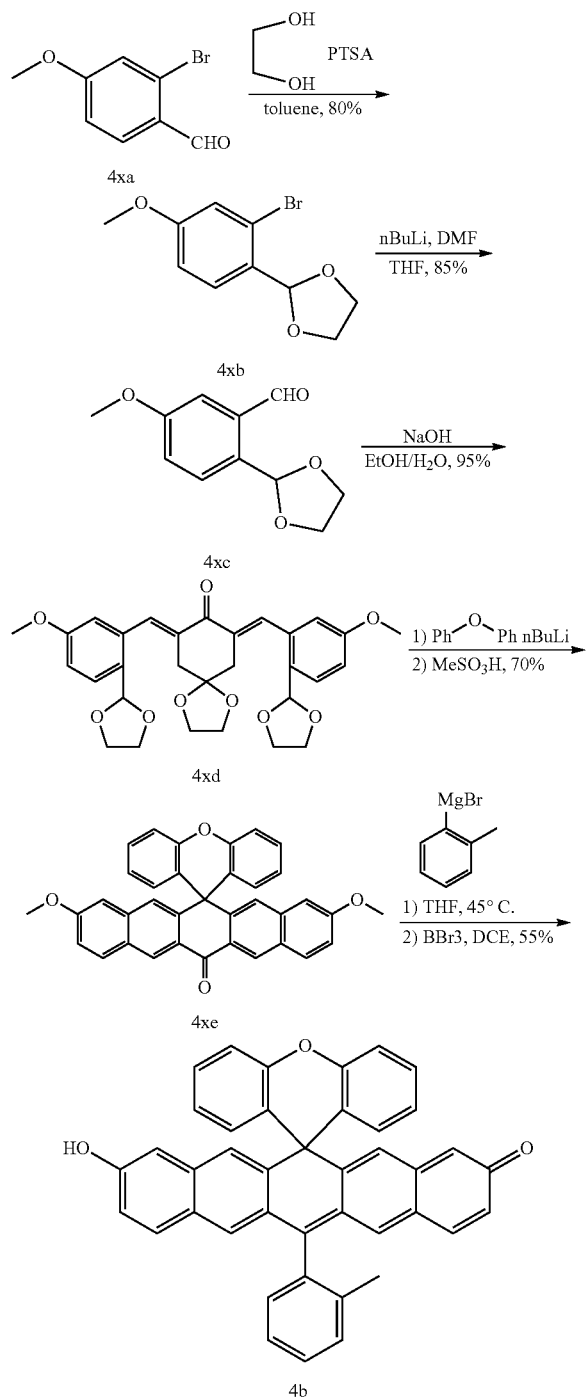

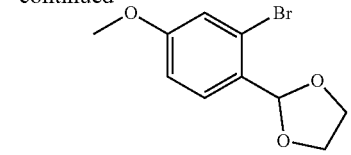

Compound 4xa (5 g, 23.25 mmol, 1 eq) and 1.5 g of ethylene glycol (25.57 mmol, 1.1 eq) and a small amount of p-toluenesulfonic acid were dissolved in toluene. The resultant mixture was heated and refluxed for 4 hours. Water produced by the reaction was removed by water separator. After completion of the reaction, toluene was removed by rotary evaporator and the remaining solution was treated with saturated $NaHCO_3$ solution, extracted with dichloromethane, dried over anhydrous magnesium sulfate and purified by column chromatography (PE/EA 100/2) to afford an oily compound 4xb (5.1 g, 85%); $^1$H NMR (400 MHz, $CDCl_3$) δ 7.38 (dd, J=8 Hz, 2.4 Hz, 1H), 6.97 (d, J=2.4 Hz, 2.4 Hz, 1H), 6.74 (d, J=8 Hz, 2.4 Hz, 1H), 5.9 (s, 1H), 4.00-3.97 (m, 2H), 3.90-3.87 (m, 2H), 3.62 (s, 3H); $^{13}$C NMR (101 MHz, $CDCl_3$) δ 160.64, 128.77, 128.70, 123.34, 118.00, 113.45, 102.54, 65.36, 55.53. HRMS (EI$^+$) Calculated ([M])$^+$, 258.9892; Found [M+H$^+$], 258.9792.

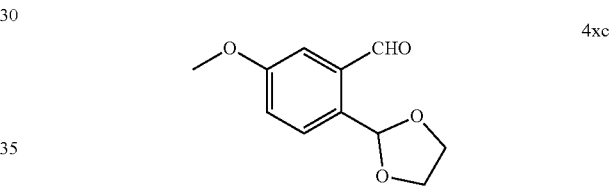

Compound 4xb (5 g, 19.3 mmol, 1 eq) was dissolved in 30 ml of anhydrous THF and 7.7 ml of n-butyllithium (2.5M, 1 eq) was added at −78° C. After reacting for 15 minutes, 1.5 g (21.2 mmol, 1.1 eq) DMF was added and the resultant mixture was slowly warmed to room temperature, quenched with saturated ammonium chloride solution, extracted with DCM, dried over anhydrous magnesium sulfate and purified by column chromatography (PE/EA 100/10) to give compound 4xc (3.42 g, 85%); $^1$H NMR (400 MHz, $CDCl_3$) δ 10.19 (s, 1H), 7.37 (d, 18 Hz, 1H), 7.20 (d, J=2.4 Hz, 1H), 6.87 (d, J=8 Hz, 2.4 Hz, 1H), 6.00 (s, 1H), 3.89-3.86 (m, 2H), 3.82-3.77 (m, 2H), 3.57 (s, 3H); $^{13}$C NMR (101 MHz, $CDCl_3$) δ 190.98, 160.14, 135.67, 131.37, 128.82, 119.21, 112.83, 101.09, 64.98, 55.15. HRMS (EI$^+$) Calculated ([M])$^+$, 208.0736; Found 208.0738.

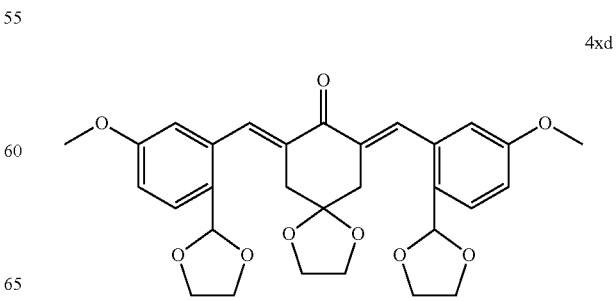

Compound 4xc (3 g, 14.41 mmol) and 1,4-cyclohexanedione monoethylene acetal (1.13 g, 7.2 mmol, 0.5 eq) were dissolved in 10 ml ethanol and 40% NaOH solution was slowly dropped into the resultant mixture. The solids in the reaction system were gradually increased. After half an hour, the reaction mixture was filtered to obtain a filter cake and then the filter cake was recrystalized with PE and EA to produce a fluffy bright yellow solid. i.e., compound 4xe (3.2 g; yield 95%). 1H NMR (400 MHz, CDCl$_3$) δ 8.07 (s, 2H), 7.51 (dd, J=8 Hz, 2.4H, 2H), 6.86 (d, J=8 Hz, 2H), 6.72 (s, 2H), 5.80 (d, J=2.4 Hz, 2H), 4.10-3.95 (m, 8H), 3.82-3.77 (m, 4H), 3.76 (s, 6H), 2.88 (s, 4H); $^{13}$C NMR (101 MHz, CDCl$_3$) δ 187.68, 159.82, 137.69, 136.50, 134.19, 128.57, 128.50, 114.52, 113.27, 106.80, 102.00, 77.56, 77.24, 76.92, 65.37, 64.64, 55.35, 37.22. HRMS (ESI$^+$) Calculated ([M])$^+$, 536.2046; Found 559.1943.

4xe

In a 100 ml round bottom flask were added 1 g (59 mmol) of diphenyl ether and 30 ml of dry THF. The flask was placed in an ice bath and 5.5 ml of n-butyllithium (c=1.6M) was added under protection of argon. After 2 hours of reaction, the whole reaction system was transferred to dry THF containing 1 g (1.5 mmol) of dissolved compound 4xd and reacted for 1 hour at normal temperature. The reaction was quenched with saturated NH$_4$Cl solution and extracted with DCM. The organic phase was separated and dried over anhydrous MgSO$_4$ solid. The solvent was removed by rotary evaporator to give a thick brown-red liquid which was separated by column chromatography (PE:EA=100:5) to give a yellow solid, i.e., compound 4xe (0.68 g), with a yield of 70%. $^1$H NMR (400 MHz, CDCl$_3$) δ8.98 (s, 2H), 7.94 (d, J=8 Hz, 2H), 7.41 (s, 2H), 7.30 (dd, J=8 Hz, 2.4H, 2H), 7.19 (t, =8 Hz, 2H), 7.12 (dd, J=8 Hz, 2.4H, 2H), 6.88 (d, f=2.4 Hz, 2H), 6.78 (t, J=8 Hz, 2H), 6.65 (dd, J=8 Hz, 2.4H, 2H), 3.82 (s, 6H); $^{13}$C NMR (101 MHz, CDCl$_3$) δ 184.01, 159.79, 149.20, 147.85, 137.91, 131.26, 131.18, 130.14, 129.15, 128.49, 127.91, 127.34, 126.54, 123.72, 120.48, 116.68, 105.11, 77.35, 77.03, 76.71, 55.36, 46.12. HRMS (ESI$^+$) Calculated ([M+Na])$^+$, 543.1572; Found 543.1571.

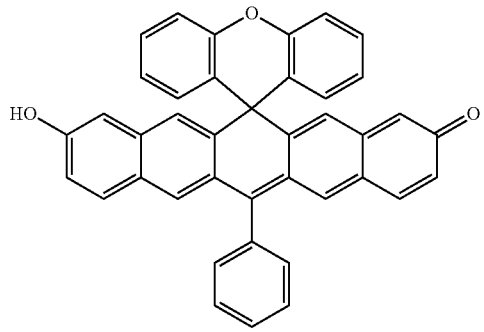

4a

Compound 4xe (50 mg) was dissolved in dry tetrahydrofuran and cooled to −78° C. Phenyl Grignard reagent was added and the resultant mixture was slowly warmed to room temperature. The reaction solution was extracted with dichloromethane and dried. BBr$_3$ in dichloromethane was added to the resultant dichloromethane solution. The resultant mixture was stirred for 30 minutes and then the reaction was quenched by water. The reaction solution was extracted by dichloromethane and dried and then subjected to column chromatography to afford compound 4a, which was a purple solid (57 mg, 51%).

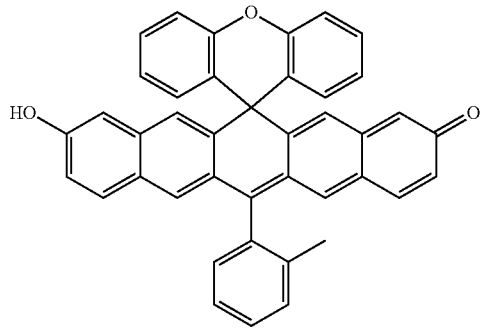

4b

Compound 4xe (50 mg) was dissolved in dry tetrahydrofuran and cooled to −78° C. O-methylphenyl Grignard reagent was added and the resultant mixture was slowly warmed to room temperature. The reaction solution was extracted with dichloromethane and dried. BBr$_3$ in dichloromethane was added to the resultant dichloromethane solution. The resultant mixture was stirred for 30 minutes and then the reaction was quenched by water. The reaction solution was extracted by dichloromethane and dried and then subjected to column chromatography to afford compound 4b, which was a purple solid (60 mg, 55%); $^1$H NMR (400 MHz, CDCl$_3$) δ 7.56 (d, J=8 Hz, 2H), 7.50 (t, J=8 Hz, 2H), 7.38 (t, J=8 Hz, 2H), 7.33 (d, J=8 Hz, 2H), 7.24-7.18 (m, 5H), 6.91 (s, 2H), 6.90-6.80 (m, 5H), 6.73 (d, J=8 Hz, 2H), 6.53 (m, 2H), 2.28 (s, 3H). HRMS (ESI$^+$) Calculated ([M+])$^+$, 567.1960; Found 567.1959.

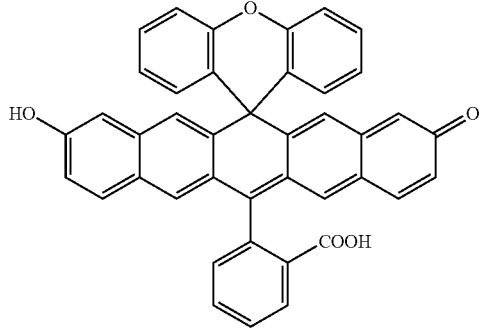

Compound 4xe (50 mg) was dissolved in dry tetrahydrofuran and cooled to −78° C. O-t-butoxylformyl phenyl Grignard reagent was added and the resultant mixture was slowly warmed to room temperature. The reaction solution was extracted with dichloromethane and dried. $BBr_3$ in dichloromethane was added to the resultant dichloromethane solution. The resultant mixture was stirred for 30 minutes and then the reaction was quenched by water. The reaction solution was extracted by dichloromethane and dried and then subjected to column chromatography to afford compound 4c, which was a purple solid (75 mg, 83%).

EXAMPLE 5

The following data are the spectral test data of compound 3d in different solvents (UV-visible data are taken from Shimadzu UV2600 UV-visible spectrometer and fluorescence data are taken from PTI QM4 fluorescence spectrometer):

| Solvent | Maximum emission wavelength (nm) | Maximum absorption wavelength (nm) | Extinction coefficient $(cm^{-1}M^{-1})$ |
|---|---|---|---|
| MeOH | 918 | 871 | 139200 |
| EtOH | 921 | 873 | 128200 |
| PrOH | 921 | 875 | 127000 |
| iPrOH | 921 | 875 | 119200 |
| BuOH | 922 | 877 | 112200 |
| Acetone | 926 | 874 | 124800 |
| DMF | 932 | 884 | 75800 |
| DMSO | 944 | 890 | 111800 |
| Pyridine | 939 | 892 | 122200 |
| DCM | 921 | 880 | 131200 |
| Chloroform | 918 | 879 | 161800 |
| Dichloroethane | 926 | 881 | 163200 |
| MeCN | 925 | 873 | 134600 |
| Benzene | 930 | 861 | 33400 |
| Toluene | 928 | 861 | 32200 |
| P-xylene | 920 | 861 | 9000 |
| Chlorobenzene | 931 | 891 | 131800 |
| Nitrobenzene | 940 | 891 | 125400 |
| 1,4-dioxane | 917 | 853 | 32200 |
| THF | 927 | 881 | 103000 |
| Ethyl acetate | 921 | 876 | 65000 |
| AcOH | 921 | 875 | 151200 |
| $H_2O$ | 925 | 787 | 49200 |

The following data are the spectral test data of different dyes in chloroform solution:

| Compound | Maximum emission wavelength (nm) | Maximum absorption wavelength (nm) | Extinction coefficient $(cm^{-1}M^{-1})$ |
|---|---|---|---|
| 1a | 864 | 836 | 217000 |
| 2a | 873 | 847 | 164000 |
| 3d | 918 | 879 | 162000 |
| 4b | 804 | 779 | 131000 |

The invention claimed is:

1. A compound of Formula A:

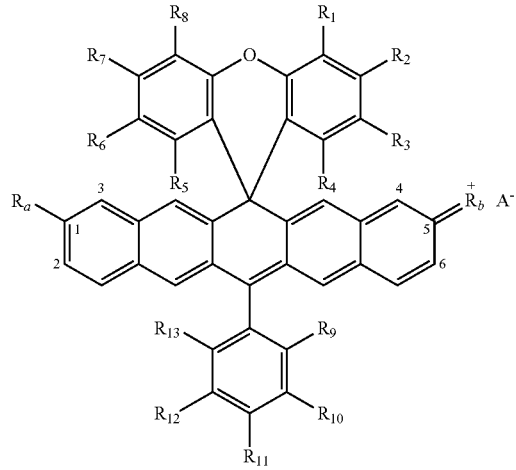

Formula A wherein:

$R_a$ is $NR_{14}R_{15}$;

$R_b$ is $NR_{14}R_{15}$;

$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl, C2-4 alkenyl, —$SO_3^-$, —$SO_2X$, —$SO_2NH_2$, nitro and C1-4 alkyl optionally substituted by one or two substituents selected from the group consisting of C1-4 alkoxyl, halogen, azido, amino and thiol;

$R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle;

X is halogen; and $A^-$ is selected from the group consisting of $F^-$, $Cl^-$, $Br^-$, $I^-$, $OAc^-$, $HSO_4^-$, $H_2PO_4^-$, $ClO_4^-$, $F_3CCOO^-$, $CH_3SO_3^-$, $CF_3SO_3^-$, $BF_4^-$, $PF_6^-$ and $NO_3^-$.

2. The compound according to claim 1, wherein the compound has a structure as shown in Formula AI, AII or AIII:

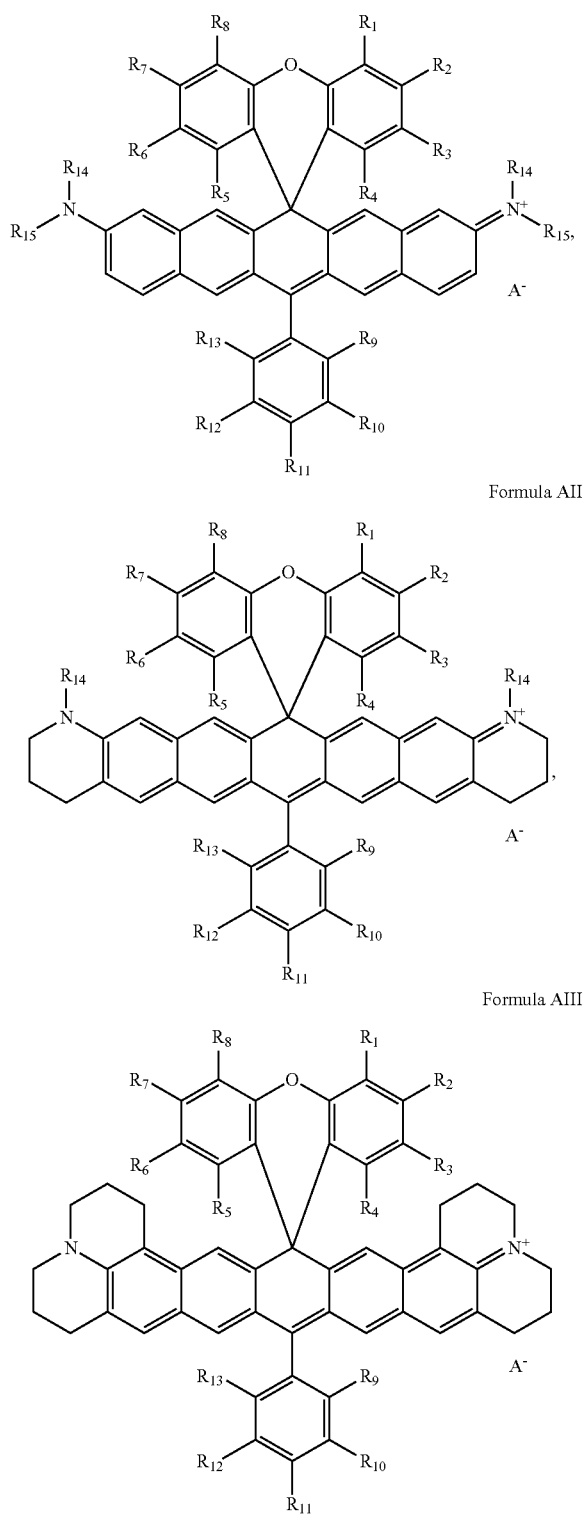

Formula AI

Formula AII

Formula AIII wherein in each of the Formulae, $R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl, C2-4 alkenyl, $-SO_3^-$, $-SO_2X$, $-SO_2NH_2$, nitro and C1-4 alkyl optionally substituted by one or two substituents selected from the group consisting of C1-4 alkoxyl, halogen, azido, amino and thiol; $R_{14}$ and $R_{15}$ are each independently selected from the group consisting of H, C1-4 alkyl and C2-4 alkenyl; and $A^-$ is those as defined in claim 1.

3. The compound according to claim 1, wherein $R_1$, $R_2$, $R_3$ and $R_4$ are each independently selected from the group consisting of H, $-SO_3^-$, $-SO_2X$ and halogen; $R_5$, $R_6$, $R_7$ and $R_8$ are each independently selected from the group consisting of H, $-SO_3^-$, $-SO_2X$ and halogen; $R_9$, $R_{10}$, $R_{11}$, $R_{12}$ and $R_{13}$ are each independently selected from the group consisting of H, $-SO_3^-$, $-SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol; or in each of the Formulae, $R_1$, $R_2$, $R_4$, $R_5$, $R_7$, $R_8$, $R_{10}$ and $R_{11}$ are H; $R_3$ is selected from the group consisting of H, $-SO_3^-$, $-SO_2X$ and halogen; $R_6$ is selected from the group consisting of H, $-SO_3^-$, $-SO_2X$ and halogen; $R_9$ is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ is selected from the group consisting of H, $-SO_3^-$, $-SO_2X$ and halogen; and $R_{13}$ is selected from the group consisting of H and C1-4 alkyl;

wherein X is halogen.

4. The compound according to claim 2, wherein in each of the Formulae, $R_1$, $R_2$, $R_3$ and $R_4$ are each independently selected from the group consisting of H, $-SO_3^-$, $-SO_2X$ and halogen; $R_5$, $R_6$, $R_7$ and $R_8$ are each independently selected from the group consisting of H, $-SO_3^-$, $-SO_2X$ and halogen; $R_9$, $R_{10}$, $R_{11}$, $R_{12}$ and $R_{13}$ are each independently selected from the group consisting of H, $-SO_3^-$, $-SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol; or in each of the Formulae, $R_1$, $R_2$, $R_4$, $R_5$, $R_7$, $R_8$, $R_{10}$ and $R_{11}$ are H; $R_3$ is selected from the group consisting of H, $-SO_3^-$, $-SO_2X$ and halogen; $R_6$ is selected from the group consisting of H, $-SO_3^-$, $-SO_2X$ and halogen; $R_9$ is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ is selected from the group consisting of H, $-SO_3^-$, $-SO_2X$ and halogen; and $R_{13}$ is selected from the group consisting of H and C1-4 alkyl;

wherein X is halogen.

5. The compound according to claim 2, wherein:

in Formula AI, $R_{14}$ and $R_{15}$ are each independently selected from the group consisting of C1-4 alkyl and C2-4 alkenyl; $R_1$, $R_2$, $R_3$ and $R_4$ are each independently selected from the group consisting of H, $-SO_3^-$, $-SO_2X$ and halogen; $R_5$, $R_6$, $R_7$ and $R_8$ are each independently selected from the group consisting of H, $-SO_3^-$, $-SO_2X$ and halogen; $R_9$, $R_{10}$, $R_{11}$, $R_{12}$ and $R_{13}$ are each independently selected from the group consisting of H, $-SO_3^-$, $-SO_2X$, halogen, carboxyl, C1-4 alkoxyl, C2-4 alkenyl and C1-4 alkyl optionally substituted by one or two substituents selected from the group consisting of C1-4 alkoxyl, halogen, azido, amino and thiol;

in Formula AII, $R_1$, $R_2$, $R_3$, $R_4$, $R_5$, $R_6$, $R_7$ and $R_8$ are H; $R_9$, $R_{10}$, $R_{11}$, $R_{12}$ and $R_{13}$ are independently selected from the group consisting of H and C1-4 alkyl;

in Formula AIII, $R_1$, $R_2$, $R_4$, $R_5$, $R_7$, $R_8$, $R_{10}$ and $R_{11}$ are H; $R_3$ is selected from the group consisting of H, —$SO_3^-$, —$SO_2X$ and halogen; $R_6$ is selected from the group consisting of H, —$SO_3^-$, —$SO_2X$ and halogen; $R_9$ is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ is selected from the group consisting of H, —$SO_3^-$, —$SO_2X$ and halogen; and $R_{13}$ is selected from the group consisting of H and C1-4 alkyl.

6. The compound according to claim 5, wherein:
in Formula AI, $R_{14}$ and $R_{15}$ are each independently selected from the group consisting of C1-4 alkyl and C2-4 alkenyl; $R_1$, $R_2$, $R_4$, $R_5$, $R_7$, $R_8$, $R_{10}$ and $R_{11}$ are H; $R_3$ is selected from the group consisting of H, —$SO_3^-$, —$SO_2X$ and halogen; R % is selected from the group consisting of H, —$SO_3^-$, —$SO_2X$ and halogen; $R_9$ is selected from the group consisting of H, carboxyl, C1-4 alkoxyl, C2-4 alkenyl and C1-4 alkyl optionally substituted by one or two substituents selected from the group consisting of C1-4 alkoxyl, halogen, azido, amino and thiol; $R_{12}$ is selected from the group consisting of H, —$SO_3^-$, —$SO_2X$ and halogen; and $R_{13}$ is selected from the group consisting of H and C1-4 alkyl;
in Formula AII, $R_1$, $R_2$, $R_3$, $R_4$, $R_5$, $R_6$, $R_7$, $R_8$, $R_{10}$, $R_{11}$, $R_{12}$ and $R_{13}$ are H; $R_9$ is selected from the group consisting of H and C1-4 alkyl.

7. The compound according to claim 5, wherein, in Formula AI, $R_{14}$ and $R_{15}$ are each independently selected from the group consisting of C1-4 alkyl and C2-4 alkenyl; $R_1$, $R_2$, $R_3$, $R_4$, $R_5$, $R_6$, $R_7$, $R_8$, $R_{10}$, $R_{11}$, $R_{12}$ and $R_{13}$ are H; $R_9$ is selected from the group consisting of H and C1-4 alkyl optionally substituted by one or two substituents selected from the group consisting of C1-4 alkoxyl and halogen.

8. A compound of Formula B:

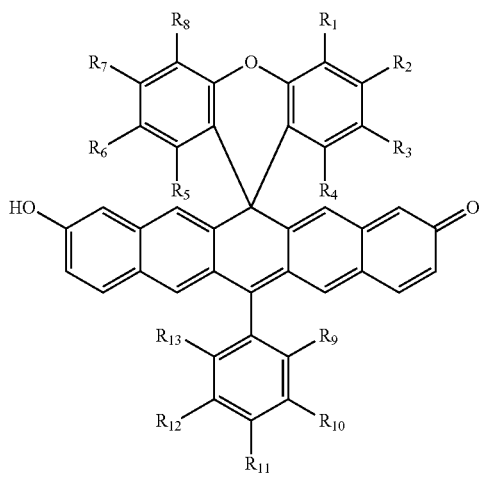

Formula B wherein:
$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl, C2-4 alkenyl, —$SO_3^-$, —$SO_2X$, —$SO_2NH_2$, nitro and C1-4 alkyl optionally substituted by one or two substituents selected from the group consisting of C1-4 alkoxyl, halogen, azido, amino and thiol, wherein X is halogen.

9. The compound according to claim 8, wherein $R_1$, $R_2$, $R_3$, $R_4$, $R_5$, $R_6$, $R_7$ and $R_8$ are H; $R_9$, $R_{10}$, $R_{11}$, $R_{12}$ and $R_{13}$ are independently selected from the group consisting of H, carboxyl and C1-4 alkyl.

10. The compound according to claim 8, wherein $R_1$, $R_2$, $R_3$, $R_4$, $R_5$, $R_6$, $R_7$, $R_8$, $R_{10}$, $R_{11}$, $R_{12}$ and $R_{13}$ are H; $R_9$ is selected from the group consisting of H, carboxyl and C1-4 alkyl.

11. A compound selected from the group consisting of:

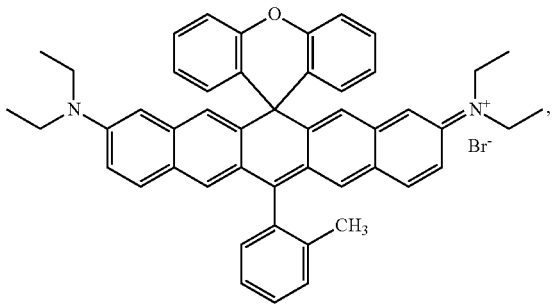

1a

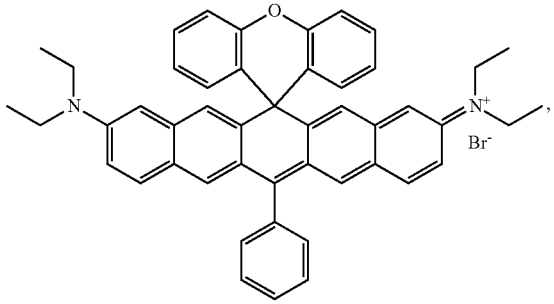

1b

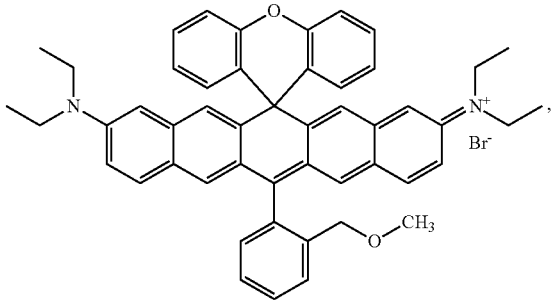

1c

1d
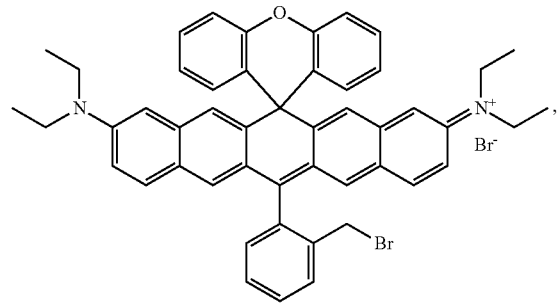
1e
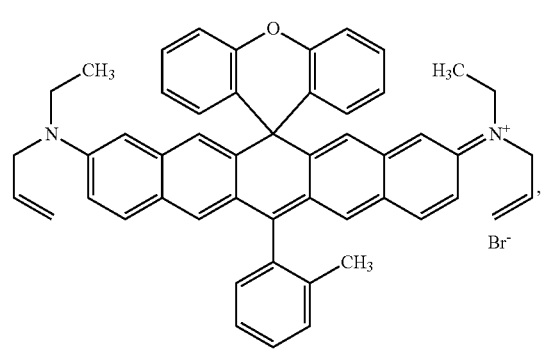
2a
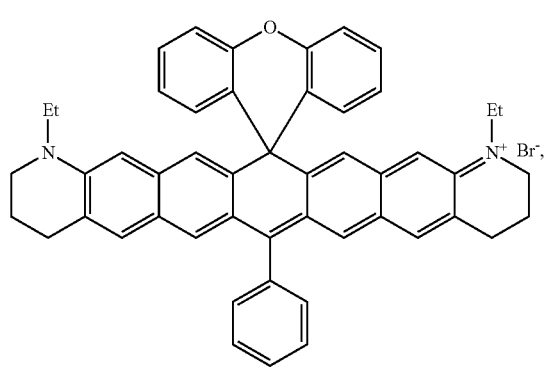
2b
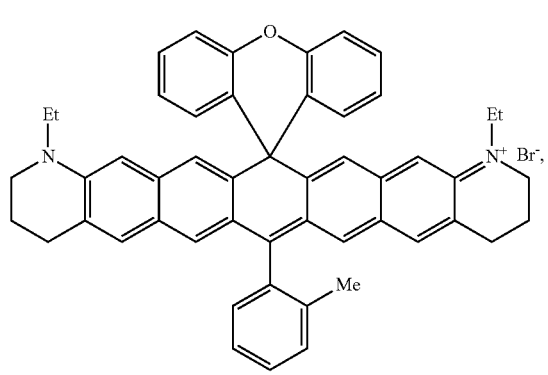
3a
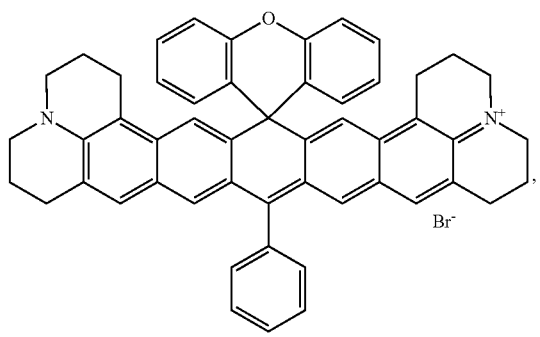
3b
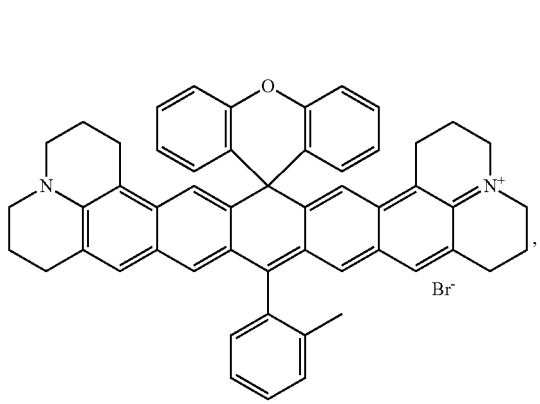
3c
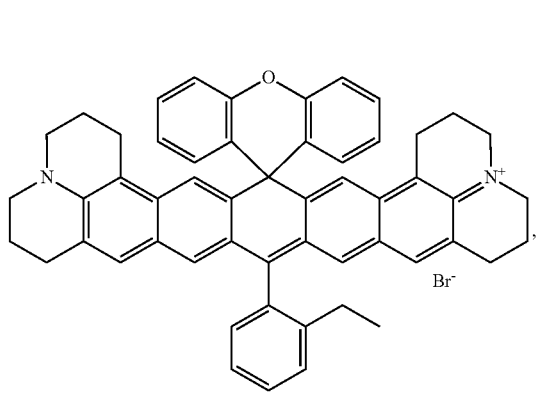
3d
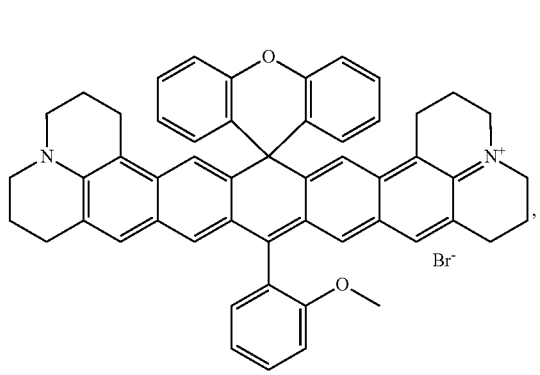

-continued
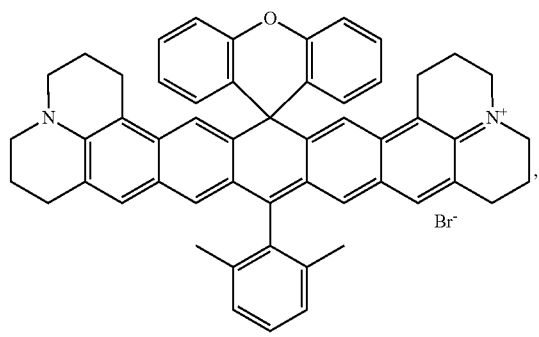
3e
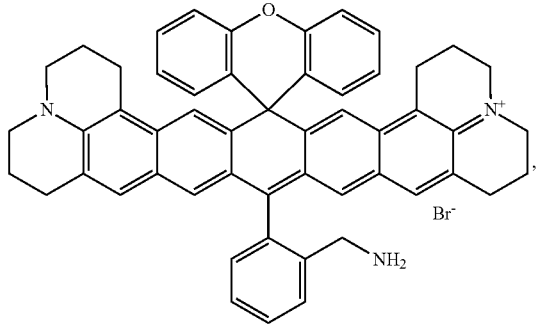
3i
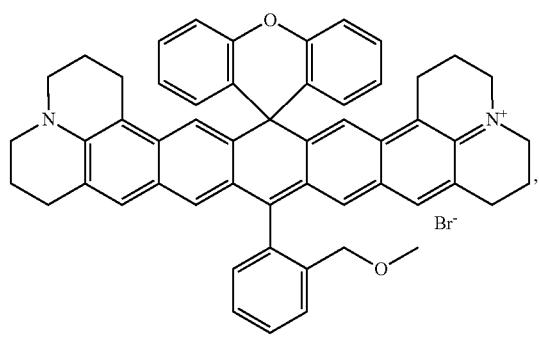
3f
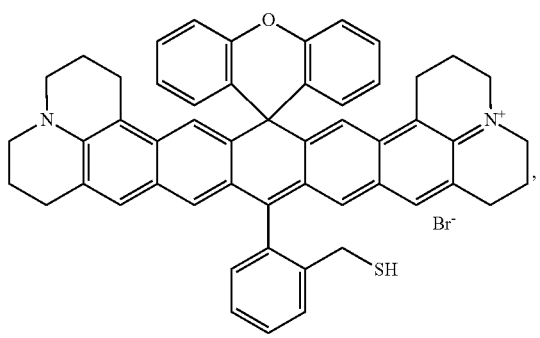
3j
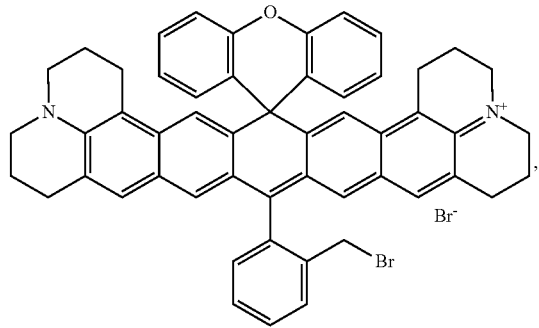
3g
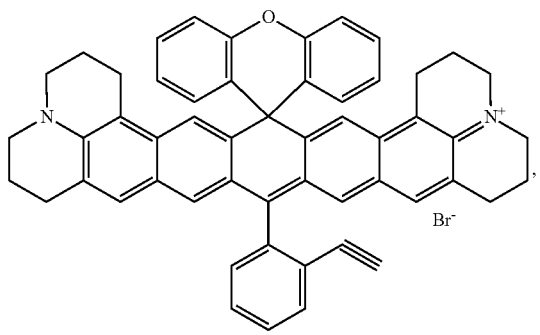
3k
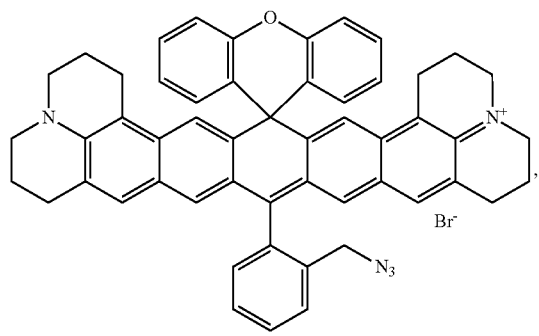
3h
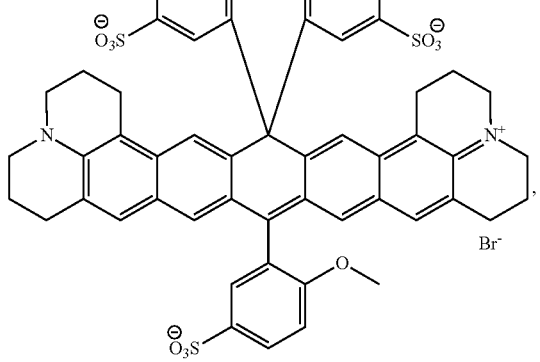
3l

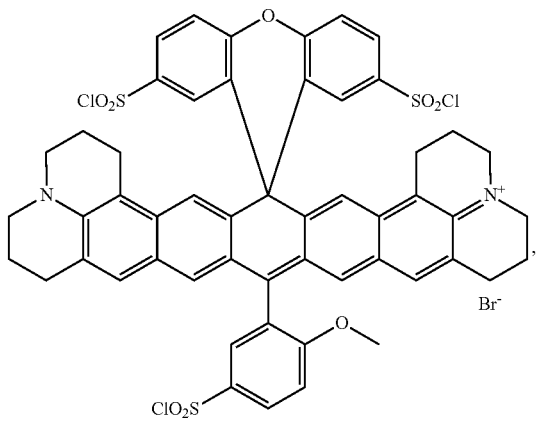

3m

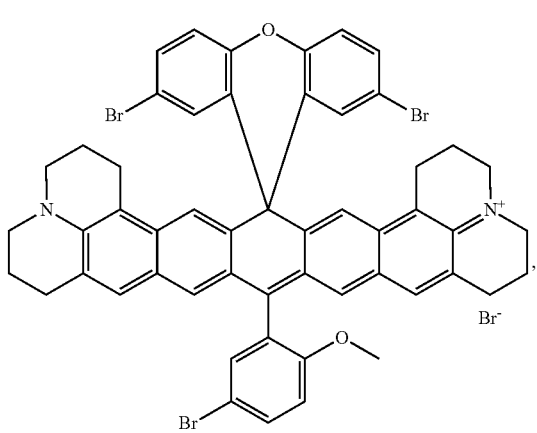

3n

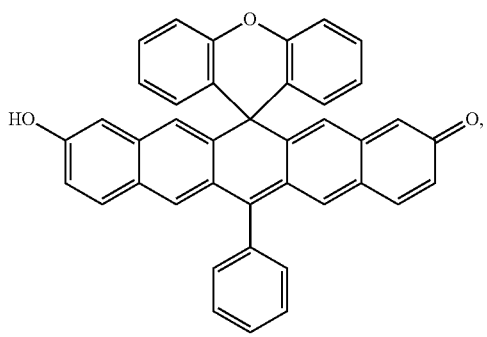

4a

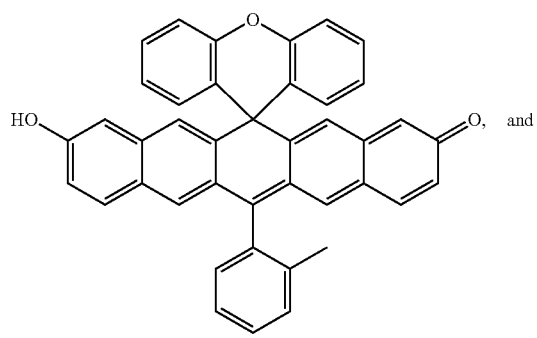

4b

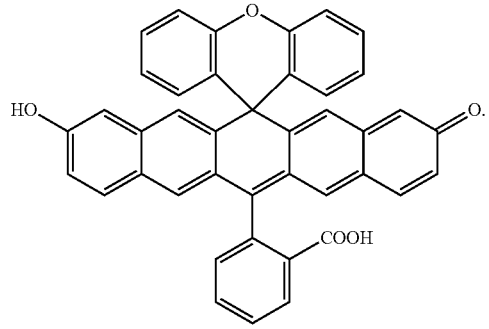

4c

12. A compound of Formula C:

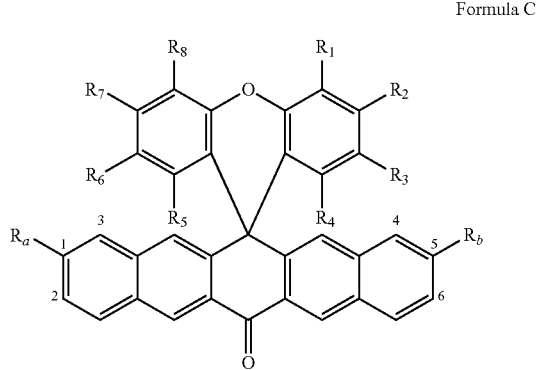

Formula C wherein $R_a$ is $NR_{14}R_{15}$ or $OR_{14}$;

$R_b$ is $NR_{14}R_{15}$ or $OR_{14}$;

$R_1$, $R_2$, $R_3$, $R_4$, $R_5$, $R_6$, $R_7$ and $R_8$ are each independently selected from the group consisting of H, hydroxyl, amino, C1-4 alkoxyl, halogen, cyano, carboxyl, C2-4 alkenyl, $-SO_3^-$, $-SO_2X$, $-SO_2NH_2$, nitro and C1-4 alkyl optionally substituted by one or two substituents selected from the group consisting of C1-4 alkoxyl, halogen, azido, amino and thiol, wherein X is halogen; and $R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle.

13. The compound according to claim 12, wherein the compound of Formula C has a structure as shown in Formula CI, CII, CIII or CIV:

Formula CI

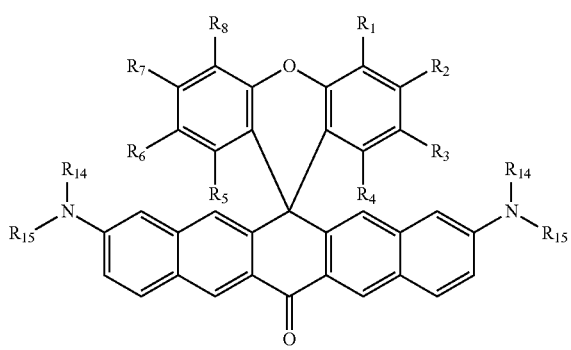

Formula CII

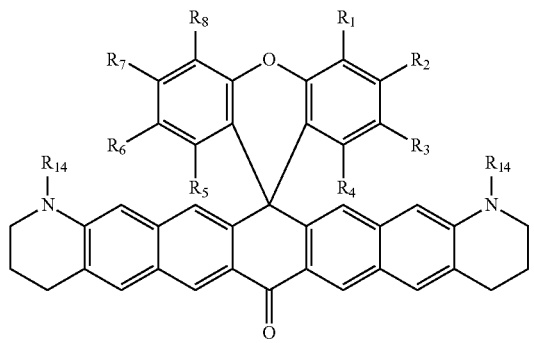

Formula CIII

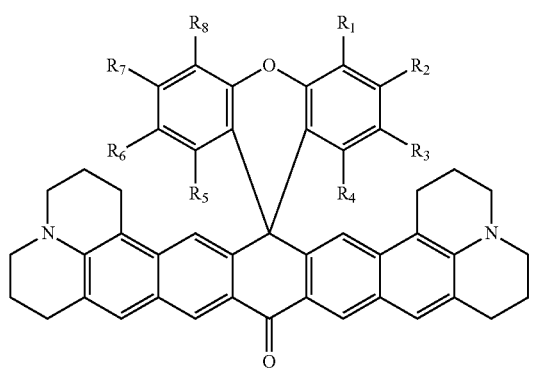

Formula CIV

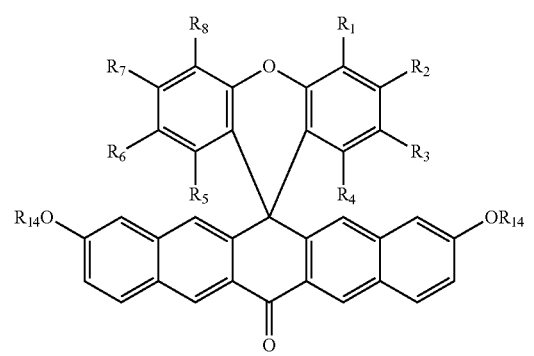

wherein $R_1$, $R_2$, $R_3$, $R_4$, $R_5$, $R_6$, $R_7$ and $R_8$ are those as defined in claim 12, $R_{14}$ and $R_{15}$ each are independently H, C1-4 alkyl or C2-4 alkenyl.

14. The compound according to claim 13, wherein, in each of the Formulae, $R_1$, $R_2$, $R_3$ and $R_4$ are each independently selected from the group consisting of H, $-SO_3^-$, $-SO_2X$ and halogen; $R_5$, $R_6$, $R_7$ and $R_8$ are each independently selected from the group consisting of H, $-SO_3^-$, $-SO_2X$ and halogen; wherein X is halogen.

15. The compound according to claim 13, wherein, in each of the Formulae, $R_1$, $R_2$, $R_4$, $R_5$, $R_7$, $R_8$ are H; $R_3$ is selected from the group consisting of H, $-SO_3^-$, $-SO_2X$ and halogen; $R_6$ is selected from the group consisting of H, $-SO_3^-$, $-SO_2X$ and halogen; wherein X is halogen.

16. A dye composition comprising:

a compound of Formula A:

Formula A

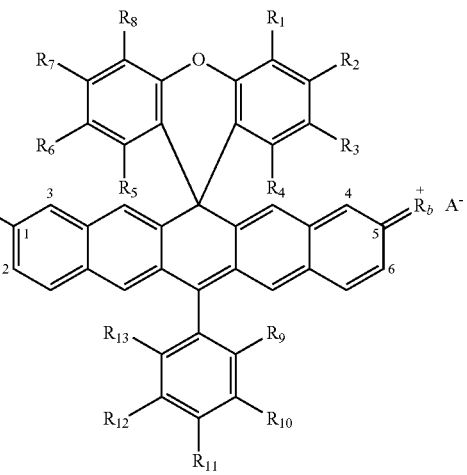

wherein:

$R_a$ is $NR_{14}R_{15}$;

$R_b$ is $NR_{14}R_{15}$;

$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl, C2-4 alkenyl, $-SO_3^-$, $-SO_2X$, $-SO_2NH_2$, nitro and C1-4 alkyl optionally substituted by one or two substituents selected from the group consisting of C1-4 alkoxyl, halogen, azido, amino and thiol;

$R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle;

X is halogen; and $A^-$ is selected from the group consisting of $F^-$, $Cl^-$, $Br^-$, $I^-$, $OAc^-$, $HSO_4^-$, $H_2PO_4^-$, $ClO_4^-$, $F_3CCOO^-$, $CH_3SO_3^-$, $CF_3SO_3^-$, $BF_4^-$, $PF_6^-$ and $NO_3^-$; or a compound of Formula B:

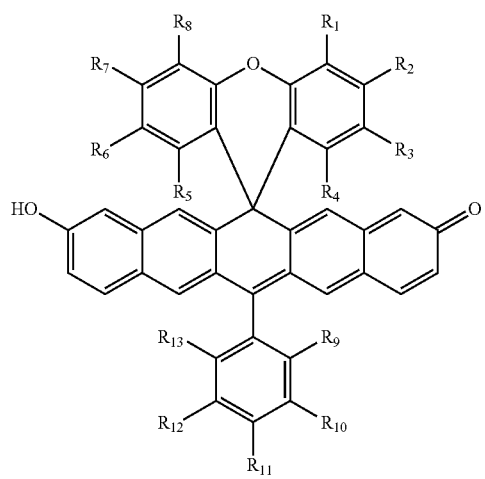

Formula B wherein:
$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl, C2-4 alkenyl, —$SO_3^-$, —$SO_2X$, —$SO_2NH_2$, nitro and C1-4 alkyl optionally substituted by one or two substituents selected from the group consisting of C1-4 alkoxyl, halogen, azido, amino and thiol, wherein X is halogen; or a compound of Formula C:

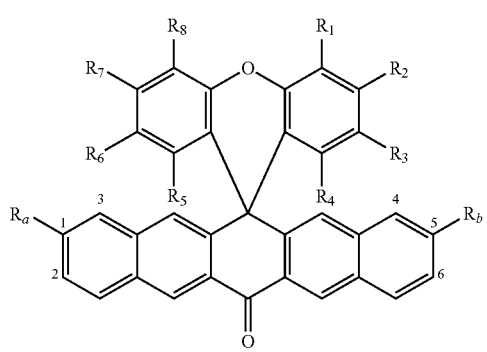

Formula C wherein:
$R_a$ is $NR_{14}R_{15}$ or $OR_{14}$;
$R_b$ is $NR_{14}R_{15}$ or $OR_{14}$;
$R_1$, $R_2$, $R_3$, $R_4$, $R_5$, $R_6$, $R_7$ and $R_8$ are each independently selected from the group consisting of H, hydroxyl, amino, C1-4 alkoxyl, halogen, cyano, carboxyl, C2-4 alkenyl, —$SO_3^-$, —$SO_2X$, —$SO_2NH_2$, nitro and C1-4 alkyl optionally substituted by one or two substituents selected from the group consisting of C1-4 alkoxyl, halogen, azido, amino and thiol, wherein X is halogen; and
$R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle.

17. A dye composition comprising a compound selected from the group consisting of:

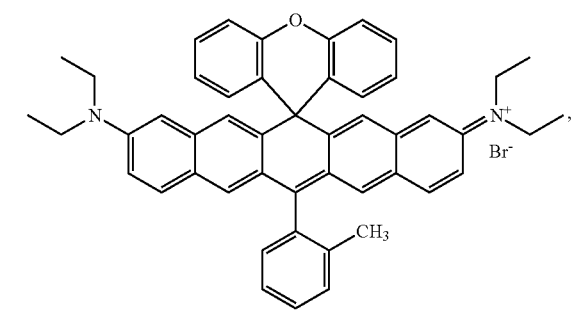

1a

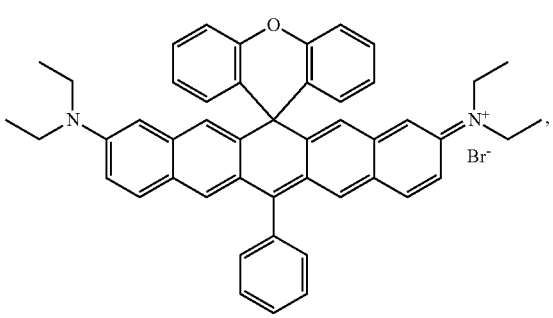

1b

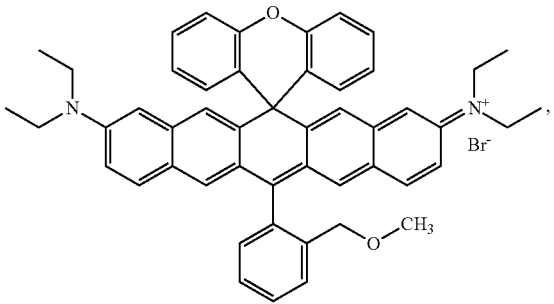

1c

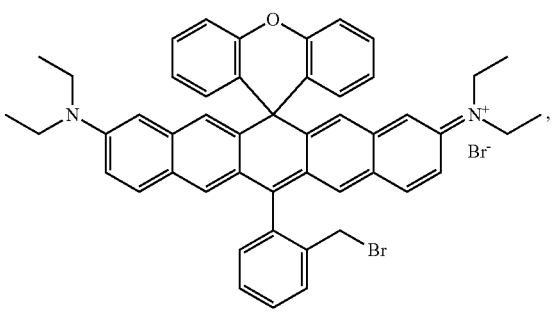

1d

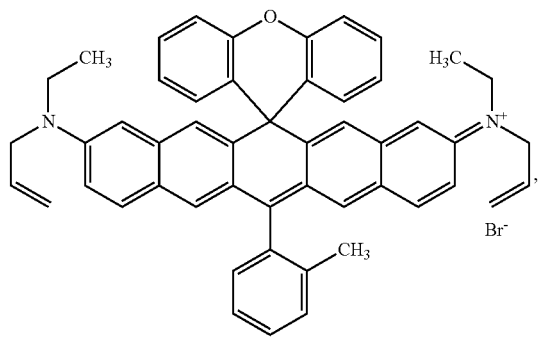
1e
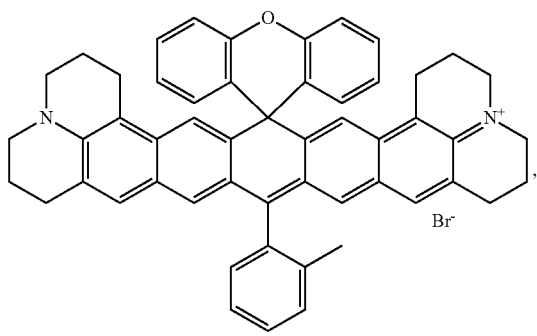
3b
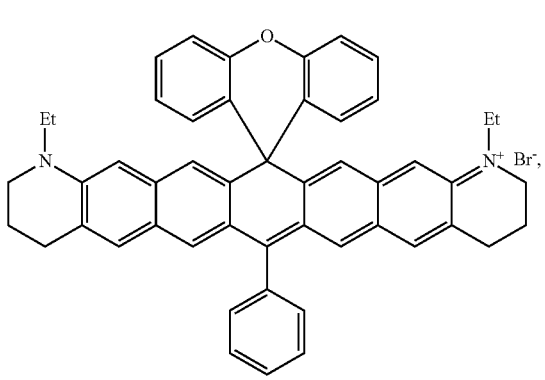
2a
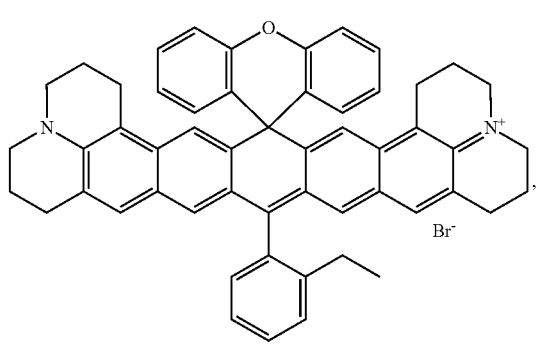
3c
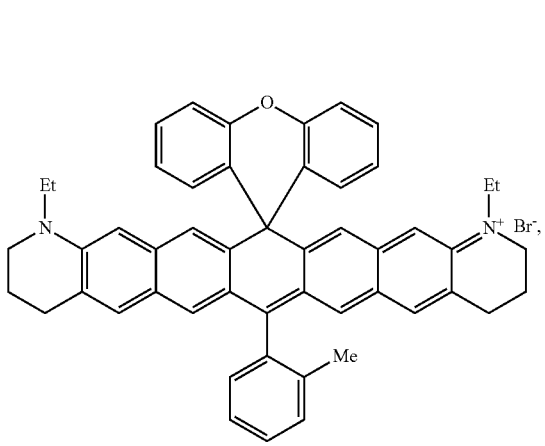
2b
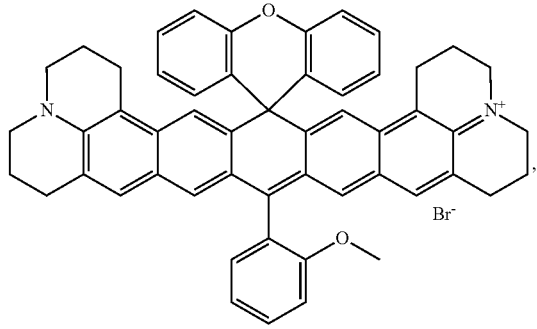
3d
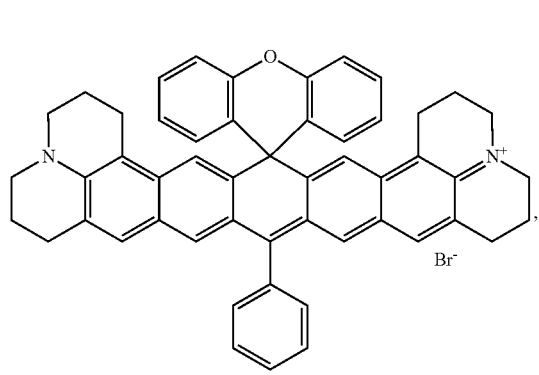
3a
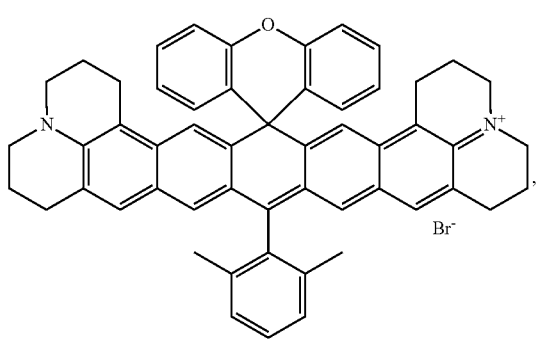
3e -continued
3f
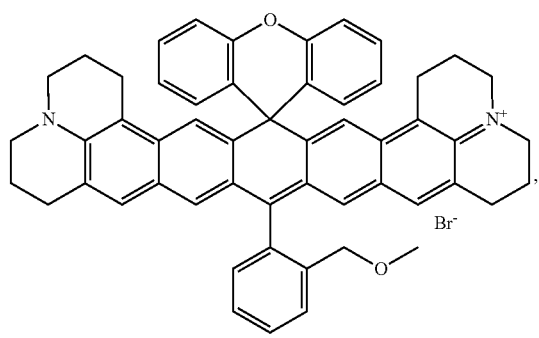
3g
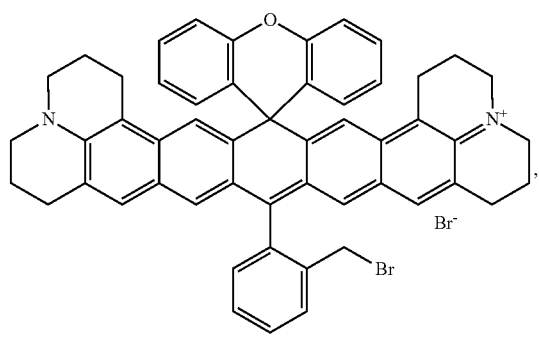
3h
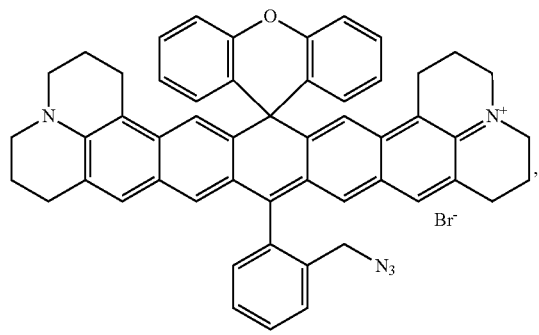
3i
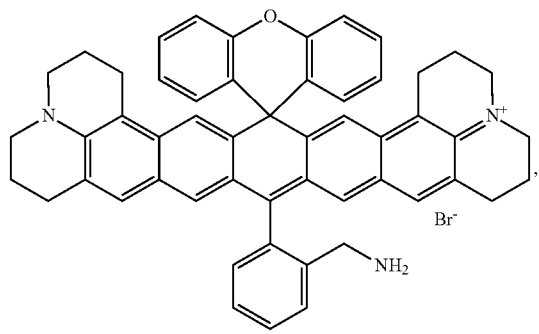
-continued
3j
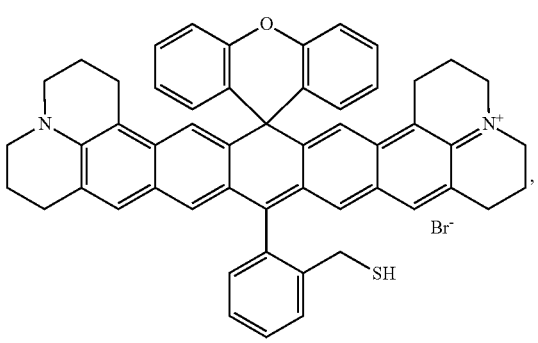
3k
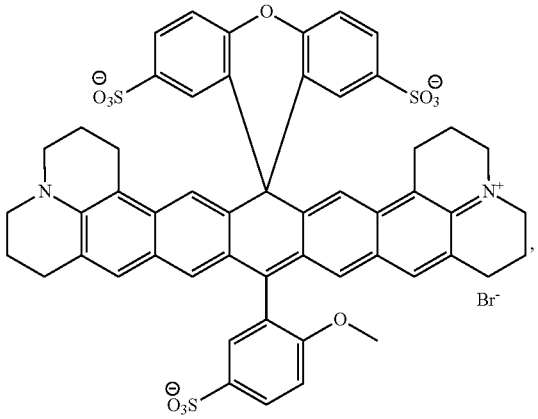
3l
3m
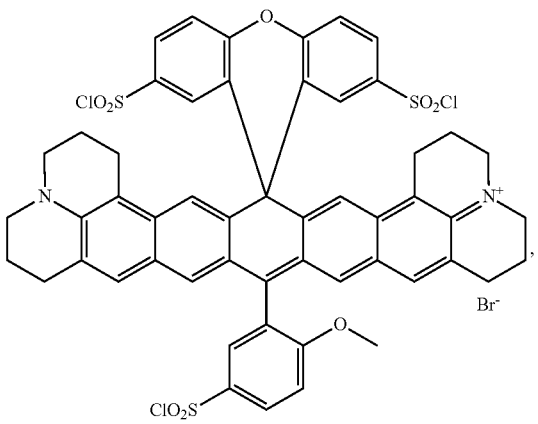

-continued

3n
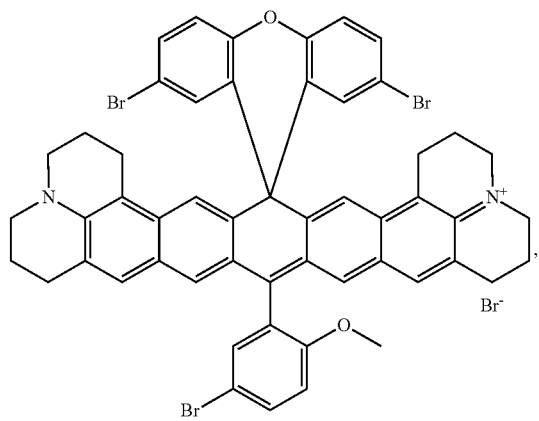

4a
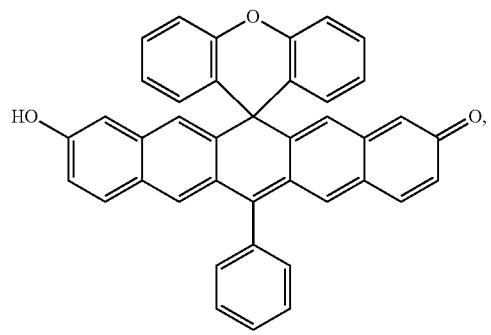

4b
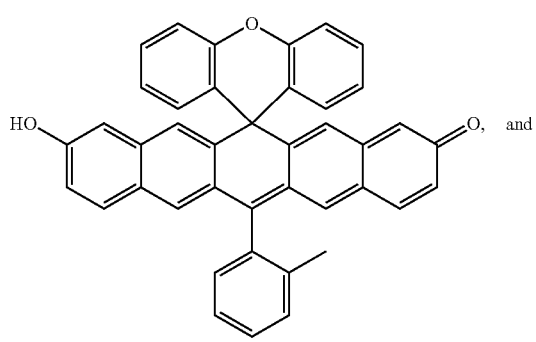

4c
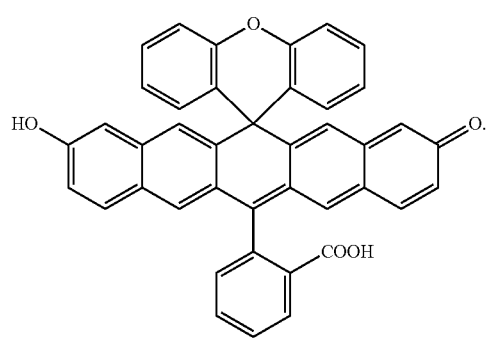

18. A method for preparing a compound of Formula A

Formula A
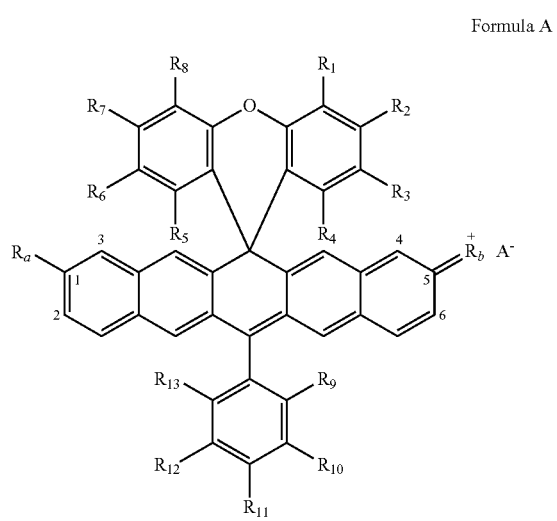

wherein:
$R_a$ is $NR_{14}R_{15}$;
$R_b$ is $NR_{14}R_{15}$;
$R_1$, $R_2$, $R_3$, $R_4$, $R_5$, $R_6$, $R_7$, $R_8$, $R_9$, $R_{10}$, $R_{11}$, $R_{12}$ and $R_{13}$ are each independently selected from the group consisting of H, hydroxyl, amino, C1-4 alkoxyl, halogen, cyano, carboxyl, C2-4 alkenyl, —$SO_3^-$, —$SO_2X$, —$SO_2NH_2$, nitro and C1-4 alkyl optionally substituted by one or two substituents selected from the group consisting of C1-4 alkoxyl, halogen, azido, amino and thiol;
$R_{14}$ and $R_{15}$ are each independently selected from the group consisting of H, C1-4 alkyl and C2-4 alkenyl; or $R_{14}$, together with N, C1 and C3 to which it attaches or together with N, C4 and C5 to which it attaches, forms a 6-membered nitrogen-containing heterocycle, and/or $R_{15}$, together with N, C1 and C2 to which it attaches or together with N, C5 and C6 to which it attaches, forms a 6-membered nitrogen-containing heterocycle;
X is halogen; and
$A^-$ is selected from the group consisting of $F^-$, $Cl^-$, $Br^-$, $I^-$, $OAc^-$, $HSO_4^-$, $H_2PO_4^-$, $ClO_4^-$, $F_3CCOO^-$, $CH_3SO_3^-$, $CF_3SO_3^-$, $BF_4^-$, $PF_6^-$ and $NO_3^-$;
comprising carrying out an addition reaction between a compound of the following Formula C and a compound of the following Formula C8 in an ether solvent, thereby producing the compound of Formula A:

Formula C
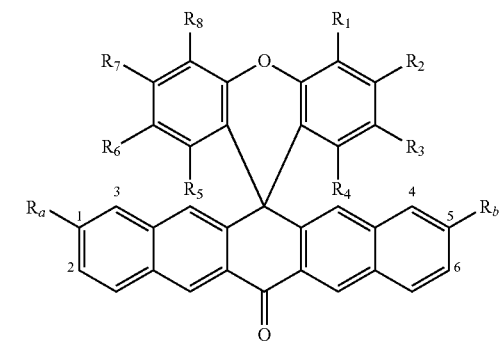

wherein:
R$_a$ is NR$_{14}$R$_{15}$ or OR$_4$;
R$_b$ is NR$_{14}$R$_{15}$ or OR$_{14}$;
R$_1$, R$_2$, R$_3$, R$_4$, R$_5$, R$_6$, R$_7$ and R$_8$ are each independently selected from the group consisting of H, hydroxyl, amino, C1-4 alkoxyl, halogen, cyano, carboxyl, C2-4 alkenyl, —SO$_3^-$, —SO$_2$X, —SO$_2$NH$_2$, nitro and C1-4 alkyl optionally substituted by one or two substituents selected from the group consisting of C1-4 alkoxyl, halogen, azido, amino and thiol, wherein X is halogen; and R$_{14}$ and R$_{15}$ are each independently selected from the group consisting of H, C1-4 alkyl and C2-4 alkenyl; or R$_{14}$, together with N, C1 and C3 to which it attaches or together with N, C4 and C5 to which it attaches, forms a 6-membered nitrogen-containing heterocycle, and/or R$_{15}$, together with N, C1 and C2 to which it attaches or together with N, C5 and C6 to which it attaches, forms a 6-membered nitrogen-containing heterocycle;

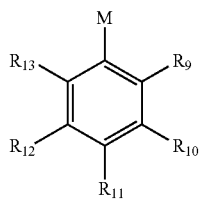

Formula C8 wherein in Formula C8, R$_9$, R$_{10}$, R$_{11}$, R$_{12}$ and R$_{13}$ are each independently selected from the group consisting of H, hydroxyl, amino, C1-4 alkoxyl, halogen, cyano, carboxyl, C2-4 alkenyl, —SO$_3^-$—SO$_2$X, —SO$_2$NH$_2$, nitro and C1-4 alkyl optionally substituted by one or two substituents selected from the group consisting of C1-4 alkoxyl, halogen, azido, amino and thiol, and M is Li or MgBr.

19. The method according to claim 18, wherein the ether solvent is ethyl ether, tetrahydrofuran, dioxane or a mixture thereof.

20. A method for preparing a compound of Formula B

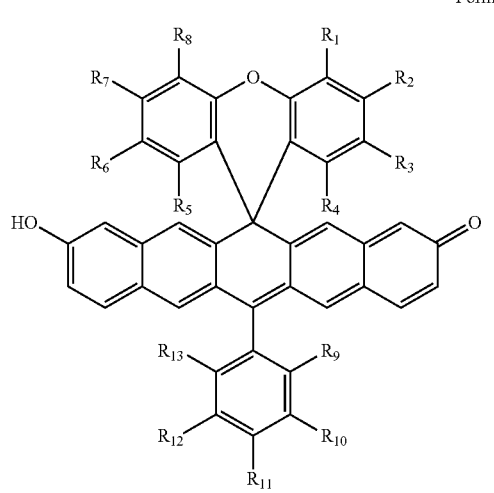

Formula B wherein:
R$_1$, R$_2$, R$_3$, R$_4$, R$_5$, R$_6$, R$_7$, R$_8$, R$_9$, R$_{10}$, R$_{11}$, R$_{12}$ and R$_{13}$ are each independently selected from the group consisting of H, hydroxyl, amino, C1-4 alkoxyl, halogen, cyano, carboxyl, C2-4 alkenyl, —SO$_3^-$, —SO$_2$X, —SO$_2$NH$_2$, nitro and C1-4 alkyl optionally substituted by one or two substituents selected from the group consisting of C1-4 alkoxyl, halogen, azido, amino and thiol, wherein X is halogen;

comprising reacting a compound of the following Formula C with a compound of the following Formula C8 in an ether solvent and then treating the product by an acid to produce the compound of Formula B:

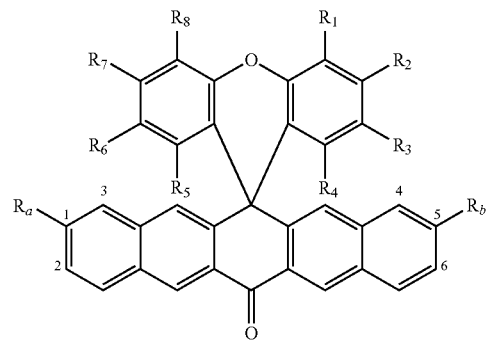

Formula C wherein:
R$_a$ is NR$_{14}$R$_{15}$ or OR$_{14}$;
R$_b$ is NR$_{14}$R$_{15}$ or OR$_{14}$;
R$_1$, R$_2$, R$_3$, R$_4$, R$_5$, R$_6$, R$_7$ and R$_8$ are each independently selected from the group consisting of H, hydroxyl, amino, C1-4 alkoxyl, halogen, cyano, carboxyl, C2-4 alkenyl, —SO$_3^-$, —SO$_2$X, —SO$_2$NH$_2$, nitro and C1-4 alkyl optionally substituted by one or two substituents selected from the group consisting of C1-4 alkoxyl, halogen, azido, amino and thiol; and R$_{14}$ and R$_{15}$ are each independently selected from the group consisting of H, C1-4 alkyl and C2-4 alkenyl; or R$_{14}$, together with N, C1 and C3 to which it attaches or together with N, C4 and C5 to which it attaches, forms a 6-membered nitrogen-containing heterocycle, and/or R$_{15}$, together with N, C1 and C2 to which it attaches or together with N, C5 and C6 to which it attaches, forms a 6-membered nitrogen-containing heterocycle;

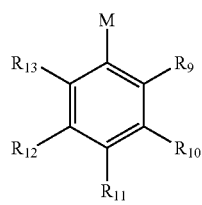

Formula C8 wherein in Formula C8, R$_9$, R$_{10}$, R$_{11}$, R$_{12}$ and R$_{13}$ are each independently selected from the group consisting of H, hydroxyl, amino, C1-4 alkoxyl, halogen, cyano, carboxyl, C2-4 alkenyl, —SO$_3^-$, —SO$_2$X, —SO$_2$NH$_2$, nitro and C1-4 alkyl optionally substituted by one or two substituents selected from the group consisting of C1-4 alkoxyl, halogen, azido, amino and thiol, and M is Li or MgBr.

21. The method according to claim 20, wherein the ether solvent is ethyl ether, tetrahydrofuran, dioxane or a mixture thereof; and the acid is selected from the group consisting of protonic acid and Lewis acid.

22. The method according ti claim 21, wherein the acid is selected from the group consisting of HBr, HI, BBr$_3$, and AlCl$_3$.

* * * * *